United States Patent
Teramoto et al.

(10) Patent No.: US 11,046,736 B2
(45) Date of Patent: Jun. 29, 2021

(54) FILAMENTOUS FUNGAL HOST

(71) Applicant: Novozymes A/S, Bagsvaerd (DK)

(72) Inventors: Hiroshi Teramoto, Chiba (JP); Kaihei Kojima, Chiba-ken (JP); Preethi Ramaiya, Sunnyvale, CA (US)

(73) Assignee: Novozymes A/S, Bagsvaerd (DK)

( * ) Notice: Subject to any disclaimer, the term of this patent is extended or adjusted under 35 U.S.C. 154(b) by 291 days.

(21) Appl. No.: 16/319,780

(22) PCT Filed: Jul. 19, 2017

(86) PCT No.: PCT/EP2017/068242
§ 371 (c)(1),
(2) Date: Jan. 22, 2019

(87) PCT Pub. No.: WO2018/015443
PCT Pub. Date: Jan. 25, 2018

(65) Prior Publication Data
US 2019/0169238 A1 Jun. 6, 2019

(30) Foreign Application Priority Data

Jul. 22, 2016 (EP) .................................... 16180774

(51) Int. Cl.
*C12N 1/14* (2006.01)
*C12N 15/80* (2006.01)
*C07K 14/38* (2006.01)
*C12P 21/02* (2006.01)

(52) U.S. Cl.
CPC .............. *C07K 14/38* (2013.01); *C12N 1/14* (2013.01); *C12N 15/80* (2013.01); *C12P 21/02* (2013.01); *C12Y 302/01003* (2013.01)

(58) Field of Classification Search
None
See application file for complete search history.

(56) References Cited

U.S. PATENT DOCUMENTS

| 2010/0093030 A1* | 4/2010 | Sagt | C12N 9/90 435/69.1 |
| 2010/0221775 A1 | 9/2010 | Penttila et al. | |
| 2019/0169238 A1* | 6/2019 | Teramoto | C12N 15/80 |

FOREIGN PATENT DOCUMENTS

| KR | 1020100133885 | * 12/2010 | ............. G01N 33/68 |
| WO | 2012087004 A2 | 6/2012 | |

OTHER PUBLICATIONS

UniProt Accession No. A2Q941_ASPNC, published Mar. 6, 2007 (Year: 2007).*
Howard et al, 1995, J Cell Biochem Suppl, 19B, 209.
Valkonen et al, 2003, Appl Environ Microbiol 69(12), 6979-6986.
Valkonen et al, 2004, Mol Genet Genom 272(4), 443-451.

* cited by examiner

*Primary Examiner* — Richard C Ekstrom
(74) *Attorney, Agent, or Firm* — Eric Fechter

(57) ABSTRACT

The instant invention relates to filamentous fungal host cells producing and secreting a heterologous polypeptide of interest, said mutant host cell comprising and expressing a mutated ireA gene or a homologue thereof encoding a modified IreA polypeptide or a homologue thereof, said modified IreA polypeptide or homologue thereof comprising amino acid substitutions in 5 positions corresponding to positions 81 and 84 in the *Aspergillus niger* IreA amino acid sequence shown in SEQ ID NO:16, as well as methods of producing a polypeptide of interest in said cells and methods for constructing said cells.

25 Claims, 3 Drawing Sheets

Specification includes a Sequence Listing.

FILAMENTOUS FUNGAL HOST

CROSS-REFERENCE TO RELATED APPLICATIONS

This application is a 35 U.S.C. § 371 national application of PCT/EP2017/068242 filed Jul. 19, 2017, which claims priority or the benefit under 35 U.S.C. § 119 of European Application No. 16180774.8 filed Jul. 22, 2016, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a modified filamentous fungal host cell having an improved productivity and/or yield of a polypeptide of interest.

BACKGROUND OF THE INVENTION

Recombinant gene expression in fungal host strain is a common method for recombinant protein production for such as enzymes and other valuable proteins. In industrial and commercial purposes, protein productivity of fungal host strains is an important factor of production costs.

It has been reported that the unfolded protein response signal transducer Ire1p promotes secretion of heterologous proteins in yeast (Howard et al. 1995, J Cell Biochem Suppl. No. 19B, p. 209). Ire1p is an endoplasmic reticulum (ER) stress sensor in all eukaryotes, and it catalyzes the splicing of had mRNA in yeast, bZIP60 in plants and xbp1 in metazoans. Hac1 and its orthologues act as transcriptional activators for transcription of unfolded protein response (UPR) related genes which have important roles for efficient expression of not only endogenous but also exogenous or recombinant proteins.

Ways of increasing the secretion of a heterologous protein in a eukaryotic cell are always of commercial interest.

SUMMARY OF THE INVENTION

*Aspergillus niger* strain C2578 produces a glucoamylase from *Penicillium oxalicum* (PoAMG) as a recombinant secreted polypeptide. The productivity/yield of PoAMG was significantly and surprisingly increased in strain C2578 by two single-nucleotide mutations in the ireA gene which encodes IreA, an orthologue of yeast Ire1. The two mutations resulted in two amino acid substitutions in IreA: Ala81Thr and Ala84Thr (A81T and A84T).

Accordingly, in a first aspect the invention relates to filamentous fungal host cells producing and secreting a heterologous polypeptide of interest, said mutant host cell comprising and expressing a mutated ireA gene or a homologue thereof encoding a modified IreA polypeptide or a homologue thereof, said modified IreA polypeptide or homologue thereof comprising amino acid substitutions in positions corresponding to positions 81 and 84 in the *Aspergillus niger* IreA amino acid sequence shown in SEQ ID NO:16.

A second aspect of the invention relates to methods of producing a polypeptide of interest, said method comprising the steps of:

a) cultivating a filamentous fungal host cell as defined in the first aspect of the invention under conditions suitable for the production and secretion of the polypeptide; and, optionally b) recovering the polypeptide of interest.

In a final aspect, the invention relates to methods of improving the productivity or yield of a secreted polypeptide of interest in a filamentous fungal host cell, said method comprising the steps of:

a) providing a filamentous fungal host cell comprising and expressing an ireA gene or a homologue thereof encoding a IreA polypeptide or a homologue thereof; and b) mutating the ireA gene or homologue thereof to provide a mutated ireA gene or homologue thereof that encodes a modified IreA polypeptide or a homologue thereof, said modified IreA polypeptide or homologue thereof comprising amino acid substitutions in positions corresponding to positions 81 and 84 in the *Aspergillus niger* IreA amino acid sequence shown in SEQ ID NO:16, whereby the productivity or yield of the secreted polypeptide of interest is improved.

Figure 1:
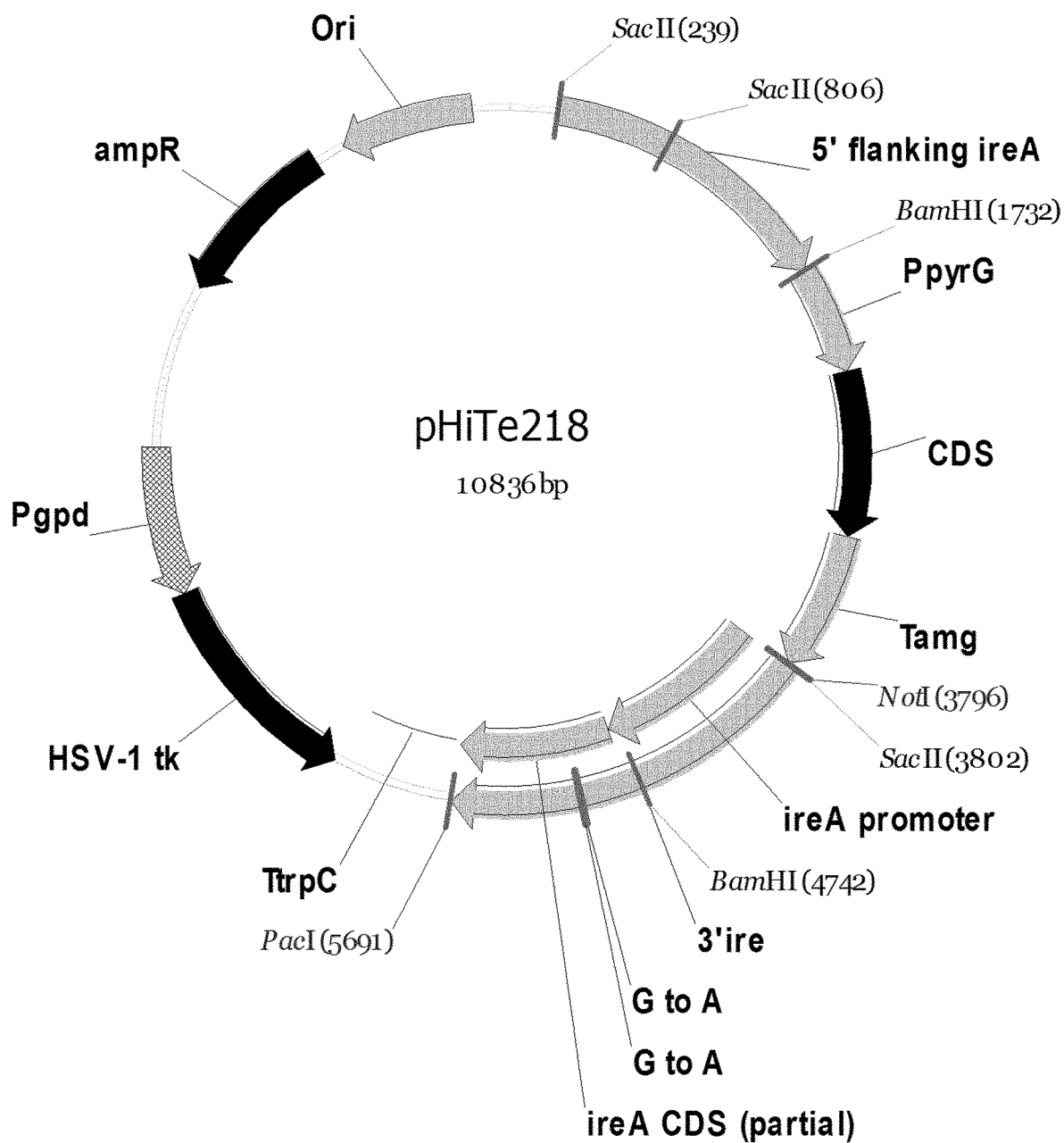
FIG. 1 shows a schematic drawing of the plasmid pHiTe218.

DEFINITIONS cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of
Alignment−Total Number of Gaps in Alignment)

DETAILED DESCRIPTION OF THE INVENTION

Host Cells

The present invention relates to recombinant host cells comprising a polynucleotide of the present invention operably linked to one or more control sequences that direct the production and secretion of a heterologous polypeptide of interest.

A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell of the invention is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonaturn, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787.

The first aspect of the invention relates to filamentous fungal host cells producing and secreting a heterologous polypeptide of interest, said mutant host cell comprising and expressing a mutated ireA gene or a homologue thereof encoding a modified IreA polypeptide or a homologue thereof, said modified IreA polypeptide or homologue thereof comprising amino acid substitutions in positions corresponding to positions 81 and 84 in the *Aspergillus niger* IreA amino acid sequence shown in SEQ ID NO:16.

In another aspect, the invention relates to methods of improving the productivity or yield of a secreted polypeptide of interest in a filamentous fungal host cell, said method comprising the steps of:
  c) providing a filamentous fungal host cell comprising and expressing an ireA gene or a homologue thereof encoding a IreA polypeptide or a homologue thereof; and
  d) mutating the ireA gene or homologue thereof to provide a mutated ireA gene or homologue thereof that encodes a modified IreA polypeptide or a homologue thereof, said modified IreA polypeptide or homologue thereof comprising amino acid substitutions in positions corresponding to positions 81 and 84 in the *Aspergillus niger* IreA amino acid sequence shown in SEQ ID NO:16, whereby the productivity or yield of the secreted polypeptide of interest is improved.

In a preferred embodiment of the aspects of the invention, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*; even more preferably the filamentous fungal host cell is an *Aspergillus* cell; preferably an *Aspergillus awamori, Aspergillus foetidus, Aspergillus fumigatus, Aspergillus japonicus, Aspergillus nidulans, Aspergillus niger* or an *Aspergillus oryzae* cell.

Preferably, the secreted polypeptide of interest is an enzyme; preferably the enzyme is a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase, or beta-xylosidase.

In a preferred embodiment, the nucleotide sequence of the mutated ireA gene or homologue thereof is at least 70% identical to the *Aspergillus niger* variant ireA nucleotide sequence shown in SEQ ID NO:17 or to its cDNA nucleotide sequence shown in SEQ ID NO:18; preferably at least 75%, 80%, 85%, 90%, 95%, 96%, 97%, 98% or most preferably at least 99% identical to the *Aspergillus niger* variant ireA nucleotide sequence shown in SEQ ID NO:17 or to its cDNA nucleotide sequence shown in SEQ ID NO:18.

In another preferred embodiment, the nucleotide sequence of the mutated ireA gene or homologue thereof encodes a variant IreA polypeptide or homologue thereof which comprises amino acid substitutions of alanine residues in positions corresponding to positions 81 and 84 in the *Aspergillus niger* IreA amino acid sequence shown in SEQ ID NO:16; preferably the alanine residues are substituted with one or more amino acid residues selected from the group of naturally occurring amino acids: alanine, arginine, asparagine, aspartic acid, cysteine, glycine, glutamic acid, glutamine, histidine, isoleucine, leucine, lysine, methionine, phenylalanine, proline, serine, threonine, tryptophan, tyrosine and valine; more preferably the alanine residues are substituted with an amino acid that does not significantly affect the folding and/or activity of the protein, a so-called conservative substitution; most preferably the alanine residues are substituted with threonine residues.

Examples of conservative substitutions are within the group of small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York.

In another preferred embodiment, the modified IreA polypeptide or homologue thereof comprises amino acid substitutions of alanine residues in positions corresponding to positions 81 and 84 in the *Aspergillus niger* IreA amino acid sequence shown in SEQ ID NO:16; preferably the alanine residues are substituted with threonine residues.

Preferably, the modified IreA polypeptide comprises an amino acid sequence at least 70% identical to SEQ ID NO:19; preferably at least 75%, 80%, 85%, 90%, 95%, 96%, 97%, 98% or most preferably at least 99% identical to SEQ ID NO:19.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Methods of Production

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

One aspect of the invention relates to methods of producing a polypeptide of interest, said method comprising the steps of:

c) cultivating a filamentous fungal host cell as defined in the first aspect of the invention under conditions suitable for the production and secretion of the polypeptide; and, optionally d) recovering the polypeptide of interest.

In a preferred embodiment, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*; even more preferably the filamentous fungal host cell is an *Aspergillus* cell; preferably an *Aspergillus awamori*, *Aspergillus foetidus*, *Aspergillus fumigatus*, *Aspergillus japonicus*, *Aspergillus nidulans*, *Aspergillus niger* or an *Aspergillus oryzae* cell.

Preferably, the secreted polypeptide of interest is an enzyme; preferably the enzyme is a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

EXAMPLES

Materials and Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for *Bacillus*". John Wiley and Sons, 1990.

Purchased Material (*E. coli* and Kits)

*E. coli* DH5α (Toyobo) was used for plasmid construction and amplification. Amplified plasmids are recovered with Qiagen Plasmid Kit (Qiagen). Ligation was done with either Rapid DNA Dephos & Ligation Kit (Roche) or In-Fusion kit (Clontech Laboratories, Inc.) according to the manufactory instructions. Polymerase Chain Reaction (PCR) is carried out with KOD-Plus system (TOYOBO). Fungal spore-PCR was conducted by using Phire® Plant Direct PCR Kit (New England Biolabs). QIAquick™ Gel Extraction Kit (Qiagen) was used for the purification of PCR fragments and extraction of DNA fragment from agarose gel.

Enzymes

Enzymes for DNA manipulations (e.g. restriction endonucleases, ligases etc.) were obtained from New England Biolabs, Inc. and were used according to the manufacturer's instructions.

Plasmids pBluescript II SK— (Stratagene #212206).

The pHUda801 plasmid harbouring *A. nidulans* pyrG gene and herpes simplex virus (HSV) thymidine kinase gene (tk) driven by *A. nidulans* glyceraldehyde-3-phosphate dehydrogenase promoter (Pgpd), *A. nidulans* tryptophane synthase terminator (TtrpC) and *A. niger* glucoamylase terminator (Tamg) was described in Example 4 and Example 5 in WO2012/160093.

The sequence of the *Penicillium oxalicum* glucoamylase (PoAMG) is described and disclosed in WO2011/127802 as SEQ ID NO: 2 therein.

Microbial Strains

The expression host strains *Aspergillus niger* C2578 and M1328 (pyrG—phenotype/uridine auxotrophy) were isolated by Novozymes and are derivatives of *Aspergillus niger* NN049184 which was isolated from soil as described in example 14 in WO2012/160093. C2578 and M1328 (pyrG—phenotype of C2578) are strains which can produce PoAMG.

Medium

COVE trace metals solution was composed of 0.04 g of $NaB_4O_7.10H_2O$, 0.4 g of $CuSO_4.5H_2O$, 1.2 g of FeSO4.7H2O, 0.7 g of MnSO4.H2O, 0.8 g of Na2MoO2.2H2O, 10 g of ZnSO4.7H2O, and deionized water to 1 liter.

50× COVE salts solution was composed of 26 g of KCl, 26 g of MgSO4.7H2O, 76 g of KH2PO4, 50 ml of COVE trace metals solution, and deionized water to 1 liter.

COVE medium was composed of 342.3 g of sucrose, 20 ml of 50× COVE salts solution, 10 ml of 1 M acetamide, 10 ml of 1.5 M CsCl2, 25 g of Noble agar, and deionized water to 1 liter.

COVE-N-Gly plates were composed of 218 g of sorbitol, 10 g of glycerol, 2.02 g of KNO3, 50 ml of COVE salts solution, 25 g of Noble agar, and deionized water to 1 liter.

COVE-N(tf) was composed of 342.3 g of sucrose, 3 g of NaNO3, 20 ml of COVE salts solution, 30 g of Noble agar, and deionized water to 1 liter.

COVE-N top agarose was composed of 342.3 g of sucrose, 3 g of NaNO3, 20 ml of

COVE salts solution, 10 g of low melt agarose, and deionized water to 1 liter.

COVE-N was composed of 30 g of sucrose, 3 g of NaNO3, 20 ml of COVE salts solution, 30 g of Noble agar, and deionized water to 1 liter.

STC buffer was composed of 0.8 M sorbitol, 25 mM Tris pH 8, and 25 mM CaCl2).

STPC buffer was composed of 40% PEG 4000 in STC buffer.

LB medium was composed of 10 g of tryptone, 5 g of yeast extract, 5 g of sodium chloride, and deionized water to 1 liter.

LB plus ampicillin plates were composed of 10 g of tryptone, 5 g of yeast extract, 5 g of sodium chloride, 15 g of Bacto agar, ampicillin at 100 μg per ml, and deionized water to 1 liter.

YPG medium was composed of 10 g of yeast extract, 20 g of Bacto peptone, 20 g of glucose, and deionized water to 1 liter.

SOC medium was composed of 20 g of tryptone, 5 g of yeast extract, 0.5 g of NaCl, 10 ml of 250 mM KCl, and deionized water to 1 liter.

TAE buffer was composed of 4.84 g of Tris Base, 1.14 ml of Glacial acetic acid, 2 ml of 0.5 M EDTA pH 8.0, and deionized water to 1 liter.

MSS is composed of 70 g Sucrose, 100 g Soybean powder (pH 6.0), water to 1 litre.

MU-1 is composed 260 g of Maltodextrin, 3 g of $MgSO_4.7H_2O$, 5 g of $KH_2PO_4$, 6 g of $K_2SO_4$, amyloglycosidase trace metal solution 0.5 ml and urea 2 g (pH 4.5), water to 1 liter.

Transformation of *Aspergillus niger*

Transformation of *Aspergillus* species can be achieved using the general methods for yeast transformation. The preferred procedure for the invention is described below.

*Aspergillus niger* host strain was inoculated to 100 ml of YPG medium supplemented with 10 mM uridine and incubated for 16 hrs at 32° C. at 80 rpm. Pellets were collected and washed with 0.6 M KCl, and resuspended 20 ml 0.6 M KCl containing a commercial β-glucanase product (GLU-CANEX™, Novozymes NS, Bagsvrd, Denmark) at a final concentration of 20 mg per ml. The suspension was incubated at 32° C. at 80 rpm until protoplasts were formed, and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml. Approximately 4 μg of plasmid DNA was added to 100 μl of the protoplast suspension, mixed gently, and incubated on ice for 30 minutes. One ml of SPTC was added and the protoplast suspension was incubated for 20 minutes at 37° C. After the addition of 10 ml of 50° C. Cove or Cove-N top agarose, the reaction was poured onto Cove or Cove-N(if) agar plates and the plates were incubated at 32° C. for 5 days.

PCR Amplifications in Examples

Polymerase Chain Reaction (PCR) was carried out with KOD-Plus system (TOYOBO).

| Component | Volume | Final Concentration |
| --- | --- | --- |
| 10× Buffer for KOD -Plus- | 5 μl | 1× |
| 2 mM dNTPs | 5 μl | 0.2 mM each |
| 25 mM MgSO$_4$ | 2 μl | 1.0 mM |
| 10 pmol/μl Primer #1 | 1.5 μl | 0.3 μM |
| 10 pmol/μl Primer #2 | 1.5 μl | 0.3 μM |
| Template DNA | X μl | |
| Genomic DNA | 10-200 ng/50 μl | |
| Plasmid DNA | 1-50 ng/50 μl | |
| PCR grade water | Y μl | |
| KOD-Plus- (1.0 U/μl) | 1 μl | 1.0 U/50 μl |
| Total reaction volume | 50 μl | |

3-Step Cycle:

| | |
| --- | --- |
| Pre-denaturation: 94° C., 2 min. | |
| Denaturation: 94° C., 15 sec. | |
| Annealing: Tm-[5-10] ° C.*, 30 sec. | 35 cycles |
| Extension: 68° C., 1 min./kb | |

Southern Hybridization

Each of the spore purified transformants were cultivated in 3 ml of YPG medium and incubated at 30° C. for 2 days with shaking at 200 rpm. Biomass was collected using a MIRACLOTH® lined funnel. Ground mycelia were subject to genome DNA preparation using FastDNA SPIN Kit for Soil (MP Biomedicals) follows by manufacture's instruction. Non-radioactive probes were synthesized using a PCR DIG probe synthesis kit (Roche Applied Science, Indianapolis Ind.) followed by manufacture's instruction. DIG labeled probes were gel purified using a QIAquick™ Gel Extraction Kit (QIAGEN Inc., Valencia, Calif.) according to the manufacturer's instructions.

Five micrograms of genome DNA was digested with appropriate restriction enzymes completely for 16 hours (40 μl total volume, 4U enzyme/μl DNA) and run on a 0.8% agarose gel. The DNA was fragmented in the gel by treating with 0.2 M HCl, denatured (0.5 M NaOH, 1.5 M NaCl) and neutralized (1 M Tris, pH7.5; 1.5 M NaCl) for subsequent transfer in 20×SSC to Hybond N+ membrane (Amersham). The DNA was UV cross-linked to the membrane and pre-hybridized for 1 hour at 42° C. in 20 ml DIG Easy Hyb (Roche Diagnostics Corporation, Mannheim, Germany). The denatured probe was added directly to the DIG Easy Hyb buffer and an overnight hybridization at 42° C. was done. Following the post hybridization washes (twice in 2×SSC, room temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker.

Shaking Flask Cultivation for Glucoamylase Production

Spores of the selected transformants were inoculated in 100 ml of MSS media and cultivated at 30° C. for 3 days with shaking (220 rpm). 10% of seed culture was transferred to MU-1 medium and cultivated at 32° C. for 7 days with shaking (220 rpm). The supernatant was obtained by centrifugation and used for sub-sequent assay.

Glucoamylase Activity

Glucoamylase activity was determined by RAG assay method (Relative AG assay, pNPG method). pNPG substrate was composed of 0.1 g of p-Nitrophenyl-α-D-glycopyranoside (Nacalai Tesque), 10 ml of 1 M Acetate buffer (pH 4.3) and deionized water to 100 ml. From each diluted sample solution, 40 ul is added to well in duplicates for "Sample". And 40 ul deionized water is added to a well for "Blank". And 40 ul of AG standard solution is added as "Reference". Using Multidrop (Labsystem), 80 ul of pNPG substrate is added to each well. After 20 minutes at room temperature, the reaction is stopped by addition of 120 ul of Stop reagent (0.1 M Borax solution). OD values are measured by microplate reader at 400 nm (Power Wave X) or at 405 nm (ELx808).

Tha RAG/ml calculation was conducted according to the following formula:

$$\frac{(S-B) \times F \times AGs}{Ss - Bs},$$

wherein
S=Sample value
F=dilution factor
B=Blank value
AGs=AG/ml of the AG standard.
Ss=Value of AG standard
Bs=Blank of AG standard Example 1 Construction of the Plasmids for Integration of Mutations in ireA Gene The purpose of this experiment is to prepare the plasmid for integration of multiple single-nucleotide mutations into native ireA gene to cause amino acid changes (Ala81Thr and Ala84Thr) in *A. niger* strains.

Construction of the Plasmid pHiTe218

Plasmid pHiTe218 was constructed to contain an ireA promoter region (5' flanking) and a partial ireA variant gene (Ala81Thr and Ala84Thr) (3' flanking) separated by the *A. nidulans* orotidine-5'-phosphate decarboxylase gene (pyrG) as a selectable marker with *A. niger* AMG terminator repeats, and the human Herpes simplex virus 1 (HSV-1) thymidine kinase gene (FIG. 1). The HSV-1 thymidine kinase gene lies 3' of the 3' flanking region of the ireA gene, allowing for counter-selection of *A. niger* transformants that do not correctly target to the ireA gene locus. The plasmid was constructed in several steps as described below.

Initially, a backbone plasmid pHiTe217 was constructed. pHiTe217 is a derivative of pHiTe199 where the second Tamg repeat has been removed. A NotI site was also introduced after the first Tamg (FIG. 1).

A PCR product containing the *A. nidulans* orotidine-5'-phosphate decarboxylase gene (pyrG) as a selectable marker with *A. niger* AMG terminator was generated using the following primers:

SEQ ID NO: 1: HTJP-671
atatacatgctctagagcggccgctggagagagttgaacctggac

SEQ ID NO: 2: HTJP-666
ctgtagcttgggatccactaaatgacgtttgtgaacag

The desired fragment was amplified by PCR in a reaction composed of approximately 100 ng of pHiTe199 as described in material and method. The reaction was incubated in a Bio-Rad® C1000 Touch™ Thermal Cycler programmed for 1 cycle at 94° C. for 2 minutes; 35 cycles each at 94° C. for 15 seconds, 55° C. for 30 seconds, and 68° C. for 2 minutes; and a 4° C. hold. The resulting 2,056 bp PCR fragment was purified by 0.8% agarose gel electrophoresis using TAE buffer, excised from the gel, and extracted using a QIAQUICK® Gel Extraction Kit.

Construction of the Gene Replacement Plasmid pHiTe199

Plasmid pHiTe199 was constructed to contain an amyR variant gene (S440E, a silent mutation on A to G at 1,338 bp of the amyR gene) and 3' flanking regions for the *Aspergillus niger* amyR gene separated by the *A. nidulans* orotidine-5'-phosphate decarboxylase gene (pyrG) as a selectable marker with *A. niger* AMG terminator repeats, and the human Herpes simplex virus 1 (HSV-1) thymidine kinase gene. The HSV-1 thymidine kinase gene lies 3' of the 3' flanking region of the amyR gene, allowing for counter-selection of *A. niger* transformants that do not correctly target to the amyR gene locus. The plasmid was constructed in several steps as described below.

Figure 2:
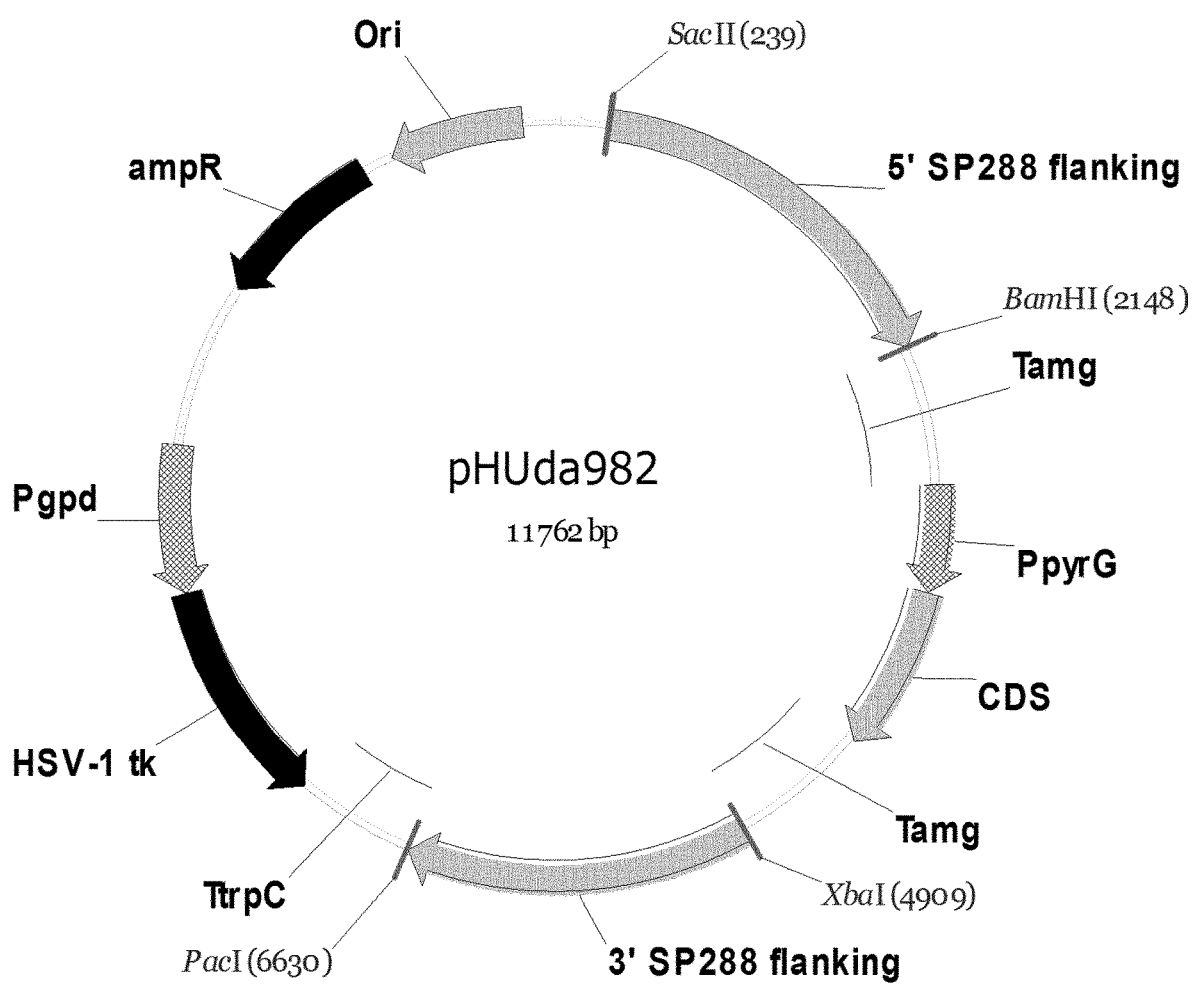
FIG. 2 shows a schematic drawing of the plasmid pHUda982.

Two PCR products containing the 5' flanking region of *A. niger* amyR were generated using the following primers:

Fragment 1    SEQ ID NO: 3: Primer
              agctggagctccaccgcggacaatgaagtctccagagtc SEQ ID NO: 4: Primer
              cgttctccaggctgagtagcacgagtcatagaaagcttc
              cacattactg Fragment 2    SEQ ID NO: 5: Primer
              tcgtgctactcagcctggagaacgcgatgaggcggttct
              tcccttca SEQ ID NO: 6: Primer
              tcagtcacccggatcccaagctacaggttctatctc The desired fragments were amplified by PCR in a reaction composed of approximately 100 ng of genome DNA of *Aspergillus niger* M1412 as described in material and method. The reaction was incubated in a Bio-Rad® C1000 Touch™ Thermal Cycler programmed for 1 cycle at 94° C. for 2 minutes; 35 cycles each at 94° C. for 15 seconds, 55° C. for 30 seconds, and 68° C. for 2 minutes; and a 4° C. hold. The resulting 1,454 bp (Fragment1) and 1,169 bp (Fragment2) PCR fragments were purified by 0.8% agarose gel electrophoresis using TAE buffer, excised from the gel, and extracted using a QIAQUICK® Gel Extraction Kit. Two fragments were fused by SOE PCR to generate the 2,603 bp insert DNA into pHUda982.

pHUda982 contains the following elements in order (FIG. 2; SEQ ID NO:7):
  5' SP288 (acid alpha-amylase: amyA: An11g03340) flanking
  *A. niger* AMG terminator (Tamg)
  PpyrG
  *A. nidulans* pyrG gene
  *A. niger* AMG terminator (Tamg)
  3' SP288 flanking pHUda982 (FIG. 2; SEQ ID NO:7) was digested with SacII and BamHI-HF (New England Biolabs Inc.), and purified by 0.8% agarose gel electrophoresis using TAE buffer, where a 9,853 bp fragment was excised from the gel and extracted using a QIAQUICK® Gel Extraction Kit. The 9,853 bp fragment was ligated to the 2,603 bp PCR fragment by using the In-Fusion kit (Clontech Laboratories, Inc.)

according to the manufactorers instructions. The reaction was performed at 50° C. for 15 minutes. One µl of the reaction mixture were transformed into DH5a chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHUda982-5'amyR-Rep.

A PCR product containing the 3' flanking region of *A. niger* amyR was generated using the following primers:

```
SEQ ID NO: 8: Primer
aactctctcctctagagcatgtatataggtgatgagac

SEQ ID NO: 9: Primer
gaattcttaattaatgtctgcattgcgcgtctac
```

The desired fragment was amplified by PCR in a reaction composed of approximately 100 ng of genome DNA of *Aspergillus niger* M1412 as described in material and method. The reaction was incubated in a Bio-Rad® C1000 Touch™ Thermal Cycler programmed for 1 cycle at 94° C. for 2 minutes; 35 cycles each at 94° C. for 15 seconds, 55° C. for 30 seconds, and 68° C. for 1 minute; and a 4° C. hold. The 546 bp PCR fragment was purified by 0.8% agarose gel electrophoresis using TAE buffer, excised from the gel, and extracted using a QIAQUICK® Gel Extraction Kit.

Figure 3:
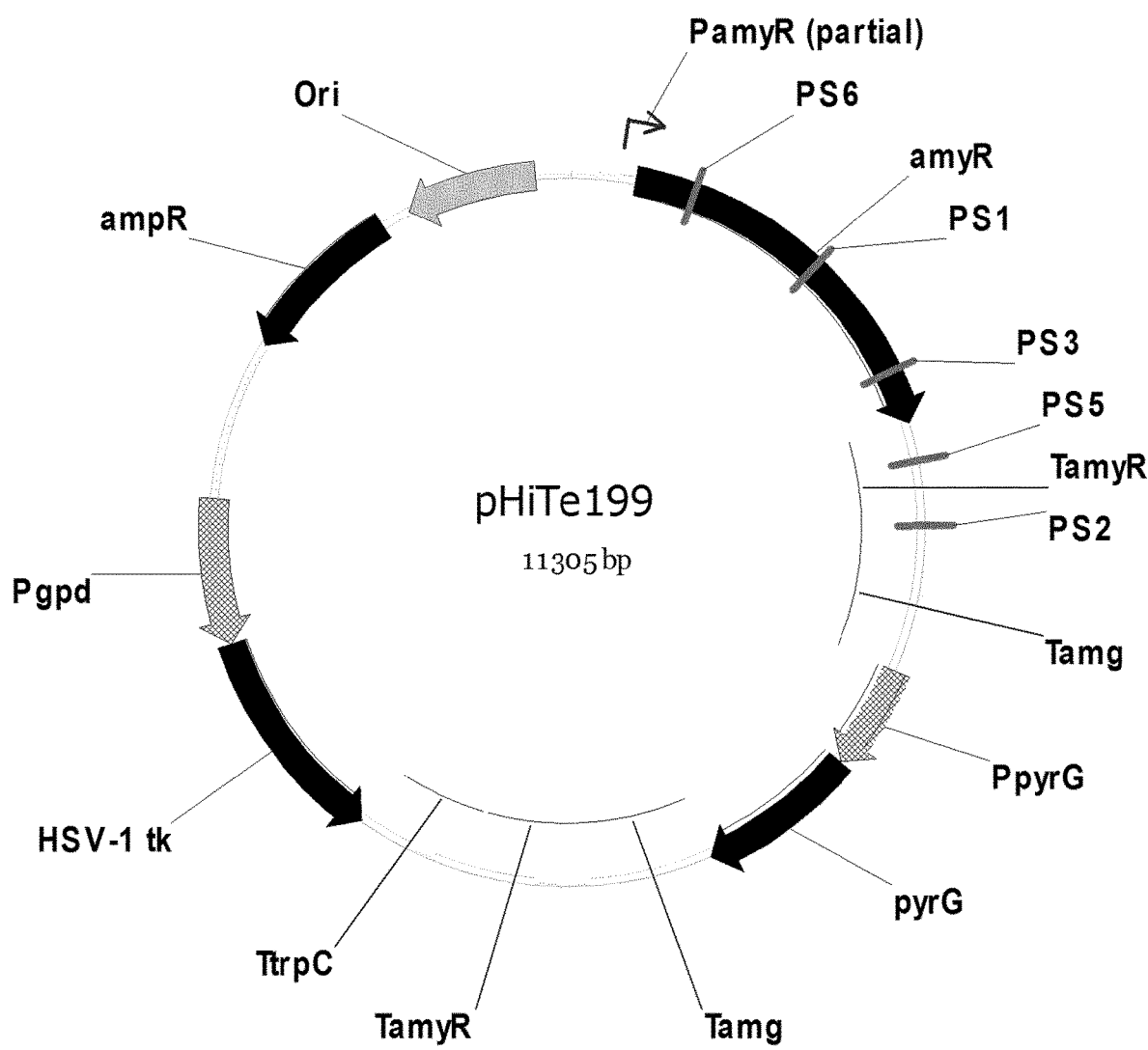
FIG. 3 shows a schematic drawing of the plasmid pHiTe199.

Plasmid pHUda982-5'amyR-Rep was digested with XbaI and PacI (New England Biolabs Inc.), and purified by 0.8% agarose gel electrophoresis using TAE buffer, where a 10,735 bp fragment was excised from the gel and extracted using a QIAQUICK® Gel Extraction Kit. The 9,536 bp fragment was ligated to the 546 bp PCR fragment by using the In-Fusion kit (Clontech Laboratories, Inc.) according to the manufactory instructions. The reaction was performed at 50° C. for 10 minutes. One µl of the ligation mixture were transformed into DH5☐ chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHiTe199 (FIG. 3).

Plasmid pHiTe199 was digested with BamHI-XbaI (New England Biolabs Inc.), and purified by 0.8% agarose gel electrophoresis using TAE buffer, where a 8,544 bp fragment was excised from the gel and extracted using a QIAQUICK® Gel Extraction Kit. The 8,544 bp fragment was ligated to the 2,056 bp PCR fragment by using the In-Fusion kit (Clontech Laboratories, Inc.) according to the manufactory instructions. The reaction was performed at 50° C. for 15 minutes. One µl of the reaction mixture were transformed into DH5α chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHiTe217.

A PCR product containing the 5'-flanking region of *A. niger* ireA was generated using the following primers:

```
SEQ ID NO: 10: HTJP-662
agctggagctccaccgcggctttcaggccttcgtaggc

SEQ ID NO: 11: HTJP-675
gtcatttagtggatcccggcagatatccactctag
```

The desired fragment was amplified by PCR in a reaction composed of approximately 100 ng of genome DNA of an *A. niger* strain harboring the 2-bp mutations on the ireA gene as described in material and method. The reaction was incubated in a Bio-Rad® C1000 Touch™ Thermal Cycler programmed for 1 cycle at 94° C. for 2 minutes; 35 cycles each at 94° C. for 15 seconds and 68° C. for 2 minutes; and a 4° C. hold. The 1,490 bp PCR fragment was purified by 0.8% agarose gel electrophoresis using TAE buffer, excised from the gel, and extracted using a QIAQUICK® Gel Extraction Kit.

pHiTe217 was digested with SacII and BamHI (New England Biolabs Inc.), and purified by 0.8% agarose gel electrophoresis using TAE buffer, where a 8,012 bp fragment was excised from the gel and extracted using a QIAQUICK® Gel Extraction Kit. The 8,012 bp fragment was ligated to the 1,490 bp PCR fragment by using the In-Fusion kit (Clontech Laboratories, Inc.) according to the manufactory instructions. The reaction was performed at 50° C. for 15 minutes. One µl of the reaction mixture were transformed into DH5a chemically competent *E. coli* cells. Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHiTe217-5'ireA-Rep.

A PCR product containing the 3'-flanking region of *A. niger* ireA was generated using the following primers:

```
SEQ ID NO: 12: HTJP-665
cctacaggagaattcttaattaaactccgagtacttgagagtg

SEQ ID NO: 13: HTJP-672
ctctctccagcggccgcggttactgccctcatacctc
```

The desired fragment was amplified by PCR in a reaction composed of approximately 100 ng of genome DNA of an *A. niger* strain harboring the 2-bp mutations on the ireA gene as described in material and method. The reaction was incubated in a Bio-Rad® C1000 Touch™ Thermal Cycler programmed for 1 cycle at 94° C. for 2 minutes; 35 cycles each at 94° C. for 15 seconds and 68° C. for 2 minutes; and a 4° C. hold. The 1,884 bp PCR fragment was purified by 0.8% agarose gel electrophoresis using TAE buffer, excised from the gel, and extracted using a QIAQUICK® Gel Extraction Kit.

pHiTe217-5'ireA-Rep was digested with NotI and PacI (New England Biolabs Inc.), and purified by 0.8% agarose gel electrophoresis using TAE buffer, where a 8,941 bp fragment was excised from the gel and extracted using a QIAQUICK® Gel Extraction Kit. The 8,941 bp fragment was ligated to the 1,884 bp PCR fragment by using the In-Fusion kit (Clontech Laboratories, Inc.) according to the manufactory instructions. The reaction was performed at 50° C. for 15 minutes. One µl of the reaction mixture were transformed into DH5α chemically competent *E. coli* cells.

Transformants were spread onto LB plus ampicillin plates and incubated at 37° C. overnight. Plasmid DNA was purified from several transformants using a QIA mini-prep kit. The plasmid DNA was screened for proper ligation by use of proper restriction enzymes followed by 0.8% agarose gel electrophoresis using TAE buffer. One plasmid was designated as pHiTe218 (FIG. 1).

Example 2 Transformation of *A. niger* Strain M1328 with pHiTe218 for the Integration of the Mutations in Endogenous ireA Gene The purpose of this experiment is to generate transformants expressing an ireA gene variant with multiple single-nucleotide substitutions in place of the wild-type genomic ireA gene shown in SEQ ID NO:14; the cDNA is shown in SEQ ID NO:15 and the encoded amino acid sequence in SEQ ID NO:16.

pHiTe218 was designed to integrate two single-nucleotide substitutions for two amino acid changes (Ala81Thr and Ala84Thr) into ireA gene by homologous recombination. The variant genomic is shown in SEQ ID NO:17; the cDNA is shown in SEQ ID NO:18 and the encoded amino acid sequence in SEQ ID NO:19.

Southern blot analysis was performed to confirm the integration of the mutations by pHiTe218 in ireA gene after transformation. Five µg of genomic DNA from each transformant were digested with NheI. The genomic DNA digestion reactions were composed of 5 µg of genomic DNA, 1 µl of NheI-HF, 2 µl of 10×NEB CutSmart buffer, and water to 20 pl. Genomic DNA digestions were incubated at 37° C. for approximately 16 hours. The digestions were submitted to 0.8% agarose gel electrophoresis using TAE buffer and blotted onto a hybond N+ (GE Healthcare Life Sciences, Manchester, N.H., USA) using a TURBOBLOTTER® for approximately 1 hour following the manufacturer's recommendations. The membrane was hybridized with a 728 bp digoxigenin-labeled *A. niger* ireA probe, which was synthesized by incorporation of digoxigenin-11-dUTP by PCR using primers HTJP-697 (sense) and HTJP-698 (antisense) shown below:

```
SEQ ID NO: 20: HTJP-697
cagcagtggcatgaacatc

SEQ ID NO: 21: HTJP-698
aggactagagtacccgaag
```

The amplification reaction (50 µl) was composed of 200 µM PCR DIG Labeling Mix (Roche Applied Science, Palo Alto, Calif., USA), 0.5 µM primers by KOD-Plus (TOYOBO) using pHUda915 as template in a final volume of 50 pl. The amplification reaction was incubated in a Bio-Rad® C1000 Touch™ Thermal Cycler programmed for 1 cycle at 94° C. for 2 minutes; 30 cycles each at 94° C. for 15 seconds, 55° C. for 30 seconds, and 68° C. for 30 seconds and a 4° C. hold. PCR products were separated by 0.8% agarose gel electrophoresis using TAE buffer where a 0.5 kb fragment was excised from the gel and extracted using a QIAQUICK® Gel Extraction Kit. The denatured probe was added directly to the DIG Easy Hyb buffer and an overnight hybridization at 42° C. was done. Following the post hybridization washes (twice in 2×SSC, room temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker. The strains, giving the correct integration at the ireA gene (a hybridized band shifted from 2.9 kb to 5.4 kb) were selected as transformants with mutations in ireA gene for Ala81Thr and Ala84Thr.

Example 3. Effect of the ireA Mutations on Productivity/Yield

Three transformants (M1328-2, M1328-6, M1328-10) from M1328 were fermented in shaking flasks and their enzyme activities (AGU activities) of culture supernatant were measured followed by the materials and methods described above; results are shown in Table 1. These three transformants expressing mutated ireA gene (Ala81Thr and Ala84Thr) showed more than 5 times higher AGU activity than the reference strain C2578 with wild-type ireA gene, showing that the mutations in ireA gene can increase enzyme productivity of a fungal host strain.

TABLE 1

The average AGU activity of the selected three strains from each host strain, wherein the average Po AMG yields from C2578 is normalized to 1.00.

| Strain | AGU relative activity |
| --- | --- |
| M1328-2 | 6.01 |
| M1328-6 | 5.18 |
| M1328-10 | 5.47 |
| C2578 | 1.00 |

The invention claimed is:

1. A filamentous fungal host cell producing and secreting a heterologous polypeptide of interest, said host cell comprising and expressing a mutated ireA gene or a homologue thereof encoding a modified IreA polypeptide or a homologue thereof, said modified IreA polypeptide or homologue thereof comprising amino acid substitutions in positions corresponding to positions 81 and 84 in the *Aspergillus niger* IreA amino acid sequence shown in SEQ ID NO:16; and wherein the nucleotide sequence of the mutated ireA gene or homologue thereof is at least 70% identical to the *Aspergillus niger* variant ireA nucleotide sequence shown in SEQ ID NO: 17 or to its cDNA nucleotide sequence shown in SEQ ID NO: 18.

2. The host cell of claim 1 which is of a genus selected from the group consisting of *Acremonium, Aspergillus, Aureobasidium, Bjerkandera, Ceriporiopsis, Chrysosporium, Coprinus, Coriolus, Cryptococcus, Filibasidium,*

*Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*.

3. The host cell of claim 2 which is an *Aspergillus* cell.

4. The host cell of claim 1, wherein the secreted polypeptide of interest is an enzyme.

5. The host cell of claim 1, wherein the modified IreA polypeptide or homologue thereof comprises amino acid substitutions of alanine residues in positions corresponding to positions 81 and 84 in the *Aspergillus niger* IreA amino acid sequence shown in SEQ ID NO: 16.

6. The host cell of claim 1, wherein the modified IreA polypeptide comprises an amino acid sequence at least 70% identical to SEQ ID NO: 19.

7. A method of producing a polypeptide of interest, said method comprising the steps of:
a) cultivating the filamentous fungal host cell of claim 1 under conditions suitable for the production and secretion of the polypeptide; and, optionally b) recovering the polypeptide of interest.

8. A method of improving the productivity or yield of a secreted polypeptide of interest in a filamentous fungal host cell, said method comprising the steps of:
a) providing a filamentous fungal host cell comprising and expressing an ireA gene or a homologue thereof encoding a IreA polypeptide or a homologue thereof; and
b) mutating the ireA gene or homologue thereof to provide a mutated ireA gene or homologue thereof that encodes a modified IreA polypeptide or a homologue thereof, said modified IreA polypeptide or homologue thereof comprising amino acid substitutions in positions corresponding to positions 81 and 84 in the *Aspergillus niger* IreA amino acid sequence shown in SEQ ID NO: 16;
wherein the nucleotide sequence of the mutated ireA gene or homologue thereof is at least 70% identical to the *Aspergillus niger* variant ireA nucleotide sequence shown in SEQ ID NO: 17 or to its cDNA nucleotide sequence shown in SEQ ID NO: 18.

9. The method of claim 8, wherein the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes* and *Trichoderma*.

10. The method of claim 9, wherein the filamentous fungal host cell is an *Aspergillus* cell.

11. The method of claim 8, wherein the secreted polypeptide of interest is an enzyme.

12. The method of claim 8, wherein the modified IreA polypeptide or homologue thereof comprises amino acid substitutions of alanine residues in positions corresponding to positions 81 and 84 in the *Aspergillus niger* IreA amino acid sequence shown in SEQ ID NO: 16.

13. The method of claim 8, wherein the modified IreA polypeptide comprises an amino acid sequence at least 70% identical to SEQ ID NO: 19.

14. The host cell of claim 1, wherein the cell is selected from *Aspergillus awamori, Aspergillus foetidus, Aspergillus fumigatus, Aspergillus japonicus, Aspergillus nidulans, Aspergillus niger* and *Aspergillus oryzae*.

15. The host cell of claim 1, wherein the secreted polypeptide of interest is a hydrolase, isomerase, ligase, lyase, oxidoreductase or transferase.

16. The host cell of claim 1, wherein the modified IreA polypeptide or homologue thereof comprises amino acid substitutions of alanine residues substituted with threonine residues in positions corresponding to positions 81 and 84 in the *Aspergillus niger* IreA amino acid sequence shown in SEQ ID NO: 16.

17. The host cell of claim 1, wherein the nucleotide sequence of the mutated ireA gene or homologue thereof is at least 80% identical to the *Aspergillus niger* variant ireA nucleotide sequence shown in SEQ ID NO: 17 or to its cDNA nucleotide sequence shown in SEQ ID NO: 18.

18. The host cell of claim 1, wherein the nucleotide sequence of the mutated ireA gene or homologue thereof is at least 90% identical to the *Aspergillus niger* variant ireA nucleotide sequence shown in SEQ ID NO: 17 or to its cDNA nucleotide sequence shown in SEQ ID NO: 18.

19. The host cell of claim 1, wherein the nucleotide sequence of the mutated ireA gene or homologue thereof is at least 95% identical to the *Aspergillus niger* variant ireA nucleotide sequence shown in SEQ ID NO: 17 or to its cDNA nucleotide sequence shown in SEQ ID NO: 18.

20. The method of claim 8, wherein the nucleotide sequence of the mutated ireA gene or homologue thereof is at least 80% identical to the *Aspergillus niger* variant ireA nucleotide sequence shown in SEQ ID NO: 17 or to its cDNA nucleotide sequence shown in SEQ ID NO: 18.

21. The method of claim 8, wherein the nucleotide sequence of the mutated ireA gene or homologue thereof is at least 90% identical to the *Aspergillus niger* variant ireA nucleotide sequence shown in SEQ ID NO: 17 or to its cDNA nucleotide sequence shown in SEQ ID NO: 18.

22. The method of claim 8, wherein the nucleotide sequence of the mutated ireA gene or homologue thereof is at least 95% identical to the *Aspergillus niger* variant ireA nucleotide sequence shown in SEQ ID NO: 17 or to its cDNA nucleotide sequence shown in SEQ ID NO: 18.

23. The method of claim 9, wherein the filamentous fungal host cell is an *Aspergillus awamori, Aspergillus foetidus, Aspergillus fumigatus, Aspergillus japonicus, Aspergillus nidulans, Aspergillus niger* or an *Aspergillus oryzae* cell.

24. The method of claim 8, wherein the secreted polypeptide of interest is a hydrolase, isomerase, ligase, lyase, oxidoreductase, or transferase.

25. The method of claim 8, wherein the modified IreA polypeptide or homologue thereof comprises amino acid substitutions of alanine residues substituted with threonine residues in positions corresponding to positions 81 and 84 in the *Aspergillus niger* IreA amino acid sequence shown in SEQ ID NO: 16.

* * * * *

SEQUENCE LISTING

<160> NUMBER OF SEQ ID NOS: 21

<210> SEQ ID NO 1
<211> LENGTH: 45
<212> TYPE: DNA
<213> ORGANISM: artificial sequence
<220> FEATURE:
<223> OTHER INFORMATION: Primer HTJP-671

<400> SEQUENCE: 1
atatacatgc tctagagcgg ccgctggaga gagttgaacc tggac        45

<210> SEQ ID NO 2

```
<211> LENGTH: 38
<212> TYPE: DNA
<213> ORGANISM: artificial sequence
<220> FEATURE:
<223> OTHER INFORMATION: Primer HTJP-666

<400> SEQUENCE: 2
ctgtagcttg ggatccacta aatgacgttt gtgaacag                              38

<210> SEQ ID NO 3
<211> LENGTH: 39
<212> TYPE: DNA
<213> ORGANISM: artificial sequence
<220> FEATURE:
<223> OTHER INFORMATION: Primer

<400> SEQUENCE: 3
agctggagct ccaccgcgga caatgaagtc tccagagtc                             39

<210> SEQ ID NO 4
<211> LENGTH: 49
<212> TYPE: DNA
<213> ORGANISM: artificial sequence
<220> FEATURE:
<223> OTHER INFORMATION: Primer

<400> SEQUENCE: 4
cgttctccag gctgagtagc acgagtcata gaaagcttcc acattactg                  49

<210> SEQ ID NO 5
<211> LENGTH: 48
<212> TYPE: DNA
<213> ORGANISM: artificial sequence
<220> FEATURE:
<223> OTHER INFORMATION: Primer

<400> SEQUENCE: 5
tcgtgctact cagcctggag aacgcgatga ggcggttctt cccttta                    48

<210> SEQ ID NO 6
<211> LENGTH: 36
<212> TYPE: DNA
<213> ORGANISM: artificial sequence
<220> FEATURE:
<223> OTHER INFORMATION: Primer

<400> SEQUENCE: 6
tcagtcaccc ggatcccaag ctacaggttc tatctc                                36

<210> SEQ ID NO 7
<211> LENGTH: 11762
<212> TYPE: DNA
<213> ORGANISM: artificial sequence
<220> FEATURE:
<223> OTHER INFORMATION: Plasmid pHUda982
<220> FEATURE:
<221> NAME/KEY: misc_feature
<222> LOCATION: (6696)..(6696)
<223> OTHER INFORMATION: n is a, c, g, or t

<400> SEQUENCE: 7
ttaatgcagc tggcacgaca ggtttcccga ctggaaagcg ggcagtgagc gcaacgcaat      60
taatgtgagt tagctcactc attaggcacc ccaggcttta cactttatgc ttccggctcg     120
tatgttgtgt ggaattgtga gcggataaca atttcacaca ggaaacagct atgaccatga     180
ttacgccaag ctcgaaatta accctcacta aagggaacaa agctggagct ccaccgcgg      240
```

```
caacaggcag aatatcttcc gaattcaatc gactgcgcga tgcaagttgg ctagcaacgg    300
cgtacacctt gggattatgc gctgctcaac cgatggtcag ctatcaaaca aaatttggga    360
agatcgggct atactgacgg tgacattata gtacggcaag ctgagtgaca tctacggtcg    420
caagccactg cttctttggg catatgtttt ctttggcgtg ggatgcatta tcaggtagat    480
actccctttt tcttatacgc tggtttgctg gttcgtgctg acagctgttt ccctagcggt    540
attggtcgag acatggcgac tgtcatattg gggcgtgcaa tcagcggaat tgggggtgct    600
ggaacaatgg cgatgggctc tatcattatc acaggtaggc tagcagctta tcaggttgaa    660
agaactgtca ctgaacatag gcagatattg ttcctcgtcg agatgttgcc cattggcggg    720
cgtacatcaa tatcgcgatg actctgggtc gtagcgcagg aggcccaatc ggcggatggc    780
taaccgatac aatcggatgg agatggtatg ctttgcgcct ttgtgaccgc ttctctcact    840
aaattgtggc caaggtcgtt tattatccaa ggccccttag ccgctgtggc agctctgttg    900
gtgatatgga agctcaaact cgccaatcca gtcactgaga gagcatccg ccgtgtcgac    960 tttctcggaa cattcctcct ggccgtcggt attgttacaa tcaccgttat catggaccaa   1020
gcagggcagt ccttcgcatg gcatcattg tcaacagcaa tccttgcaac tctcagtcta   1080
tcagcattcg tcgccttcgt ccttgttgaa ctctacgtag cccctgaacc gattttcgaa   1140
cttcgcatgt tgcggaagcc gaatgtgacg cccagttacc tgatcggatc gctgcagatc   1200
accgcccaag ttggaatgat gttctccgtg ccgttatatt ttcaggtgac atcgaaagcc   1260
tctgccaccg tagctggagg gcatctggtt cctgcagtga tcggaaacac gcttggcggc   1320
ttaatcgcgg gagcctttat ccgtcgcacc ggccaattca aggtcctctt gatccttgcc   1380
ggtctcgttg cgtccgtcgc ctatctactc ctcatccttc gctggaacgg tcatactgga   1440
ttctgggagt ccttgtacat tattcccggt ggtatgggta ctggtttctg ctctgcagct   1500
gcttttgtca gtatgacggc gttttttgatg ccgcaggaag tggccatggc aacaggaggt   1560
tacttcctat tattcagctt cgccatgacg gccggtgtca ctgtcactaa cagtctgctg   1620
gggacggttt tcaagcgcca gatggaacag cacctgacgg gtccaggagc caagaaggtt   1680
ggtatccccg cacctttct gcgtcactta ctaacgagta tatgaagatc atcgagcgcg   1740
cgctgtccga caccagctat atcaacggtt gcagggtca tgtccgggat gtagtggtaa   1800
aaggatatgt gactggtctc cgctacactt actgtaagtc gtttgaatca tgcatccacc   1860 gtccaccta ttaacttggt gccagtattt tccctcattc tttcgctcct tggatcggtc   1920
ctcgcttgga ctgtacgaaa acaccaacta tgaggaacca gcacggcagc tgatagtatc   1980
cgaaagctgc aaattgcttc atcgaggctg gcattcgata gaagaaagaa ctatagacaa   2040
ctagtcttac aatatgacaa ttctctttga ttaataaatg aaaataacac ttgtgtcagc   2100
ctaatagccg agtggcgggc atctctggcg gcctcccgag cagcgtggat ccgggtgact   2160
gacacctggc ggtagacaat caatccattt cgctatagtt aaaggatggg gatgagggca   2220
attggttata tgatcatgta tgtagtgggt gtgcataata gtagtgaaat ggaagccaag   2280
tcatgtgatt gtaatcgacc gacggaattg aggatatccg gaaatacaga caccgtgaaa   2340
gccatggtct ttccttcgtg tagaagacca gacagacagt ccctgattta cccttgcaca   2400
aagcactaga aaattagcat tccatccttc tctgcttgct ctgctgatat cactgtcatt   2460
caatgcatag ccatgagctc atcttagatc caagcacgta attccatagc cgaggtccac   2520
agtggagcag caacattccc catcattgct ttccccaggg gcctcccaac gactaaatca   2580
```

```
agagtatatc tctaccgtcc aatagatcgt cttcgcttca aaatctttga caattccaag    2640
agggtcccca tccatcaaac ccagttcaat aatagccgag atgcatggtg gagtcaatta    2700
ggcagtattg ctggaatgtc ggggccagtt ggccgggtgg tcattggccg cctgtgatgc    2760
catctgccac taaatccgat cattgatcca ccgcccacga ggcgcgtctt tgcttttttgc   2820
gcggcgtcca ggttcaactc tctcctctag tactaaatga cgtttgtgaa cagcccaaag    2880
cctacaaatt caactgcgca caacgcgccc acggcaactt cctcgagaac gcgccgcaga    2940
caatgctctc tatcctggtg gcaggcgtca agtacccaga ggcagcagcg ggcttaggag    3000
cggcctgggt tgttctccgc accctctaca tgctgggcta tatttatagc gacaagccga    3060
acggcaccgg caggtacaat ggttcgctgt acttgcttgc gcaagcgggt ctttggggat    3120
tgagcgcatt tggtgttgca aaggatttga tgtaaatgta gtcgacatct tagcacagag    3180
gggagagttg ataaaatgtg gtctgtttga atgatagtcg ggttcgtgac ctatattcgt    3240
gatagtggag ataggtctgc gcctatctta tcgggccgga gcaaaaattc caccgcagcg    3300
gggtgagttt tcgttataca gccatcccac ttccagcttc aaattgtcag tttaatccag    3360
cccaattcaa tcattggaga accgccatca tgtcttcgaa gtcccacctc ccctacgcaa    3420
ttcgcgcaac caaccatccc aacccttaa catctaaact cttctccatc gccgaggaga    3480
agaaaaccaa cgtcaccgtc tccgcagacg ttactacttc cgccgagctc ctcgatcttg    3540
ctgaccgcct aggcccctat atcgcagttc tgaaaaccca catcgacatc ctcaccgatc    3600
tcaccccgtc gacccttccc tcgctccaat ccctcgcgac aaagcacaac ttcctcatct    3660
ttgaggaccg caagttcatc gacatcggca acaccgtgca aaagcagtac cacggtggcg    3720
ctctccgcat ctccgaatgg gcacacatca tcaactgcgc catcctgccg ggcgaaggga    3780
tcgtcgaggc cctcgcacag acaaccaagt ctcctgactt taaagacgcg aatcaacgag    3840
gtctcctgat tcttgccgag atgacgagta agggatctct tgcgacaggg gagtacacgg    3900
cacgctcggt tgagtacgcg cggaagtata aggggtttgt gatgggattc gtgagtacaa    3960
gggcgttgag tgaggtgctg cccgaacaga aagaggagag cgaggatttt gtcgtcttta    4020
cgactggggt gaatctgtcg gataagggggg ataagctggg gcagcagtat cagacacctg    4080
ggtcggcggt tgggcgaggt gcggacttta tcattgcggg tagggcatc tataaggcgg     4140
acgatccagt cgaggcggtt cagaggtacc gggaggaagg ctggaaagct tacgagaaaa    4200
gagttggact ttgagggtga ctgacacctg gcggtagaca atcaatccat ttcgctatag    4260
ttaaaggatg gggatgaggg caattggtta tatgatcatg tatgtagtgg gtgtgcataa    4320
tagtagtgaa atggaagcca agtcatgtga ttgtaatcga ccgacggaat tgaggatatc    4380
cggaaataca gacaccgtga aagccatggt cttttccttcg tgtagaagac cagacagaca    4440
gtccctgatt taccctttgca caaagcacta gaaaattagc attccatcct tctctgcttg    4500
ctctgctgat atcactgtca ttcaatgcat agccatgagc tcatcttaga tccaagcacg    4560
taattccata gccgaggtcc acagtggagc agcaacattc cccatcattg ctttccccag    4620
gggcctccca acgactaaat caagagtata tctctaccgt ccaatagatc gtcttcgctt    4680
caaaatcttt gacaattcca agagggtccc catccatcaa acccagttca ataatagccg    4740
agatgcatgg tggagtcaat taggcagtat tgctggaatg tcggggccag ttggccgggt    4800
ggtcattggc cgcctgtgat gccatctgcc actaaatccg atcattgatc caccgcccac    4860
gaggcgcgtc tttgcttttt gcgcggcgtc caggttcaac tctctcctct agagaatgca    4920
atcataacag aaagtacagc cagcgctgtg tcataaagaa gtccagttgg gaaacgaaag    4980
```

```
actagaatca aactaaaagt aatccggccg atatggcttc acgtgcgaag tctcgccttg   5040 agggacatt  gtccttgcag gtgattgacc attgcgttca tatggcgcga tgtttggtag   5100
tgtgggtgta gccggtgacc tcacggaagg actaaaggcc acatacccct ctgagtgcct   5160
cttctcttcg tggtcggaac tctcgaatgg gtttttgaca gttgcactcg tttggttgtg   5220
gtcatttgaa ggtctgcgtt cggtcttctg ttcgcgcagg cgagctgact gagggattga   5280
aagctgcata gccatcgttg gcatgcgtta attcgccaaa gctcagcggc gaaacaggcc   5340
tgacctctaa tccatgcatc tgctctgcac tcgattgttc gtggtgtcct tgcgaagaaa   5400
gagaagcctt ggactcggat gactttctgg acgaggtggt aggatcatca tgattgtaat   5460
gagactgtag cacatcatgc gaatcattcg acacacggtg tctgcccaag ttgacgtcag   5520
catcggtatg catttcggta tggtcctcat ggttctcagc atgtccctcc agagggact   5580 catttccagc ggaaggatta taagcaacat aattgtcatg tggctgcgac ctttcgtgag   5640
actccgagtt tgatctcact gtggactcat gggcgatatg cggctcatca tgatcttcga   5700
atggagagaa atggttgaag tcggaggaca cgggtgattt agcagcaggg ttgaatgcaa   5760
catagccagt ctcgcgctct tcatgtgagc tatatgagtc atgtggcctg tcatggtcca   5820
gaggctccgg atgctcatgg ctagattcat cgtgtgccga aatcgcgtca ctagcaaagg   5880
gcgaggttga cacattggct gcaggactga acgccacata accactctca ggctcttcat   5940
gtgagttata ggagctgtgc ggcatatcat agtcctgagg ttcacgatgc tcatggctgg   6000
attcatcgtg tgccgaaata gcgtgactag caaaaggcga gggcgaagca ttggttgccg   6060
gactgaacgc cacatagccg tccccattgg ctgaactgac tggtgacaac gtcctaccca   6120
tggcgtcggc cgggccagcg gcttggtgag agtgaagacc attagaagta gctggactga   6180
acgatcgcag cgggtattcg ttttcttgag ctggataagg ggctgcgcca tgctggctga   6240
aaggtgagaa tgttcggggt gctgctctat caccagggaa ggcagacgct ggagtcaaag   6300
aacgagtgtt ggatcaattg ccggactgta tgaacgaaaa ggagtgctga ttgtttaaat   6360
ggcccgtagc cttcgctagg acctcgtgat tcggggaccg ttggcccata cccaggagct   6420
ggtgtaaaat tggaacgcga cacgggtgtt tggttgcgca gaatttgcgg tgccggcgag   6480
gcgtgatcaa tctggctgta acctgggcct ggggtgtagt ttgagacagg tgtttgtgtt   6540
cgtggcattt gtggcgctgg cgacgctctg tcagtcggcc catatccagg cgccgaaggt   6600
gtgggcgtaa acccttgccg tgatttaatt aagaattctc ctgtaggctt gagagttcaa   6660
ggaagaaaca gtgcaattat ctttgcgaac ccaggngctg gtgacggaat tttcatagtc   6720
aagctatcag agtaaagaag aggagcatgt caaagtacaa ttagagacaa atatatagtc   6780
gcgtggagcc aagagcggat tcctcagtct cgtaggtctc ttgacgaccg ttgatctgct   6840
tgatctcgtc tcccgaaaat gaaaatagac tctgctaagc tattcttctg cttcgccgga   6900
gcctgaaggg cgtactaggg ttgcgaggtc caatgcatta atgcattgca gatgagctgt   6960
atctggaaga ggtaaacccg aaacgcgttt tattcttgtt gacatggagc tattaaatca   7020
ctagaaggca ctcttttgctg cttggacaaa tgaacgtatc ttatcgagat cctgaacacc   7080
atttgtctca actccggagc tgacatcgac accaacgatc ttatatccag attcgtcaag   7140
ctgtttgatg atttcagtaa cgttaagtgg atcgatccgg atagcgcggg ttccttccgg   7200
tattgtctcc ttccgtgttt cagttagcct ccccatctc ccgggcaaac gtgcgcgcca   7260
ggtcgcatat cgtcggtatg gagccggggg tggtgacgtg ggtctggacc atcccggagg   7320
```

-continued

```
taagttgcag cagggcgtcc cggcagccgg cgggcgattg gtcgtaatcc aggataaaga   7380
cgtgcatgga acggaggcgt ttggccaaga cgtccaaggc ccaggcaaac acgttataca   7440
ggtcgccgtt gggggccagc aactcggggc cccgaaacag ggtaaataac gtgtccccga   7500
tatggggtcg tgggcccgcg ttgctctggg gctcggcacc ctggggcggc acggccgtcc   7560
ccgaaagctg tccccagtcc tcccgccacg acccgccgca ctgcagatac cgcaccgtat   7620
tggcaagtag cccgtaaacg cggcgaatcg cagccagcat agccaggtcc agccgctcgc   7680
cggggcgctg gcgtttggcc aggcggtcga tgtgtctgtc ctccggaagg gccccaagca   7740
cgatgttggt gccgggcaag gtcggcggga tgagggccac gaacgccagc acggcctggg   7800
gggtcatgct gcccataagg taccgcgcgg ccgggtagca caggagggcg gcgatgggat   7860
ggcggtcgaa gatgagggtg agggccgggg gcggggcatg tgagctccca gcctcccccc   7920
cgatatgagg agccagaacg gcgtcggtca cggcataagg catgcccatt gttatctggg   7980
cgcttgtcat taccaccgcc gcgtccccgg ccgatatctc accctggtcg aggcggtgtt   8040
gtgtggtgta gatgttcgcg attgtctcgg aagcccccag cacccgccag taagtcatcg   8100
gctcgggtac gtagacgata tcgtcgcgcg aacccagggc caccagcagt tgcgtggtgg   8160
tggttttccc catcccgtgg ggaccgtcta tataaacccg cagtagcgtg ggcattttct   8220
gctccgggcg gacttccgtg gcttcttgct gccggcgagg gcgcaacgcc gtacgtcggt   8280
tgctatggcc gcgagaacgc gcagcctggt cgaacgcaga cgcgtgttga tggccggggt   8340
acgaagccat acgcgcttct acaaggcgct ggccgaagag gtgcgggagt ttcacgccac   8400
caagatcgat ctacagctgg tggggagagc aggaaaatat ggcaacaaat gttggactga   8460
cgcaacgacc ttgtcaaccc cgccgacaca ccgggcggac agacggggca agctgcctac   8520
ccagggactg agggacctca gcaggtcgag tgcagagcac cggatgggtc gactgccagc   8580
ttgtgttccc ggtctgcgcc gctggccagc tcctgagcgg cctttccggt ttcatacacc   8640
gggcaaagca ggagaggcac gatatttgga cgccctacag atgccggatg gccaattag   8700 ggagcttacg cgccgggtac tcgctctacc tacttcggag aaggtactat ctcgtgaatc   8760
ttttaccaga tcggaagcaa ttggacttct gtacctaggt taatggcatg ctatttcgcc   8820
gacggctata caccctggc ttcacattct ccttcgctta ctgccggtga ttcgatgaag   8880
ctccatattc tccgatgatg caatagattc ttggtcaacg agggggcacac cagccttttcc   8940 acttcggggc ggaggggcgg ccggtcccgg attaataatc atccactgca cctcagagcc   9000
gccagagctg tctggcgcag tggccgttat tactcagccc ttctctctgc gtccgtccgt   9060
ctctccgcat gccagaaaga gtcaccggtc actgtacaga gctcaagctt cgattaactc   9120
gagggggggc ccggtaccca attcgcccta tagtgagtcg tattacaatt cactggccgt   9180
cgttttacaa cgtcgtgact gggaaaaccc tggcgttacc caacttaatc gccttgcagc   9240 acatcccccct ttcgccagct ggcgtaatag cgaagaggcc cgcaccgatc gcccttccca   9300
acagttgcgc agcctgaatg gcgaatggaa attgtaagcg ttaatatttt gttaaaattc   9360
gcgttaaatt tttgttaaat cagctcattt tttaaccaat aggccgaaat cggcaaaatc   9420
ccttataaat caaagaata gaccgagata ggggttgagtg ttgttccagt ttggaacaag   9480
agtccactat taaagaacgt ggactccaac gtcaaagggc gaaaaaccgt ctatcagggc   9540
gatggcccac tacgtgaacc atcaccctaa tcaagttttt tggggtcgag gtgccgtaaa   9600
gcactaaatc ggaaccctaa agggagcccc cgatttagag cttgacgggg aaagccggcg   9660
aacgtggcga gaaaggaagg gaagaaagcg aaaggagcgg gcgctagggc gctggcaagt   9720
```

```
gtagcggtca cgctgcgcgt aaccaccaca cccgccgcgc ttaatgcgcc gctacagggc    9780
gcgtcaggtg gcacttttcg gggaaatgtg cgcggaaccc ctatttgttt attttttctaa   9840 atacattcaa atatgtatcc gctcatgaga caataaccct gataaatgct tcaataatat    9900
tgaaaaagga agagtatgag tattcaacat ttccgtgtcg cccttattcc cttttttgcg    9960
gcattttgcc ttcctgtttt tgctcaccca gaaacgctgg tgaaagtaaa agatgctgaa   10020
gatcagttgg gtgcacgagt gggttacatc gaactggatc tcaacagcgg taagatcctt   10080
gagagttttc gccccgaaga acgttttcca atgatgagca cttttaaagt tctgctatgt   10140
ggcgcggtat tatcccgtat tgacgccggg caagagcaac tcggtcgccg catacactat   10200
tctcagaatg acttggttga gtactcacca gtcacagaaa agcatcttac ggatggcatg   10260
acagtaagag aattatgcag tgctgccata accatgagtg ataacactgc ggccaactta   10320
cttctgacaa cgatcggagg accgaaggag ctaaccgctt ttttgcacaa catgggggat   10380
catgtaactc gccttgatcg ttgggaaccg gagctgaatg aagccatacc aaacgacgag   10440
cgtgacacca cgatgcctgt agcaatggca acaacgttgc gcaaactatt aactggcgaa   10500
ctacttactc tagcttcccg gcaacaatta atagactgga tggaggcgga taaagttgca   10560
ggaccacttc tgcgctcggc ccttccggct ggctggttta ttgctgataa atctggagcc   10620
ggtgagcgtg ggtctcgcgg tatcattgca gcactggggc cagatggtaa gccctcccgt   10680
atcgtagtta tctacacgac ggggagtcag gcaactatgg atgaacgaaa tagacagatc   10740
gctgagatag gtgcctcact gattaagcat tggtaactgt cagaccaagt ttactcatat   10800
atactttaga ttgatttaaa acttcatttt taatttaaaa ggatctaggt gaagatcctt   10860
tttgataatc tcatgaccaa aatcccttaa cgtgagtttt cgttccactg agcgtcagac   10920
cccgtagaaa agatcaaagg atcttcttga gatcctttt ttctgcgcgt aatctgctgc   10980
ttgcaaacaa aaaaaccacc gctaccagcg gtggtttgtt tgccggatca agagctacca   11040
actctttttc cgaaggtaac tggcttcagc agagcgcaga taccaaatac tgtccttcta   11100
gtgtagccgt agttaggcca ccacttcaag aactctgtag caccgcctac atacctcgct   11160
ctgctaatcc tgttaccagt ggctgctgcc agtggcgata gtcgtgtct taccgggttg   11220 gactcaagac gatagttacc ggataaggcg cagcggtcgg gctgaacggg gggttcgtgc   11280
acacagccca gcttggagcg aacgacctac accgaactga gatacctaca gcgtgagcta   11340
tgagaaagcg ccacgcttcc cgaagggaga aaggcggaca ggtatccggt aagcggcagg   11400
gtcggaacag gagagcgcac gagggagctt ccagggggaa acgcctggta tctttatagt   11460
cctgtcgggt ttcgccacct ctgacttgag cgtcgatttt tgtgatgctc gtcagggggg   11520
cggagcctat ggaaaaacgc cagcaacgcg gccttttac ggttcctggc cttttgctgg   11580
ccttttgctc acatgttctt tcctgcgtta tcccctgatt ctgtggataa ccgtattacc   11640
gcctttgagt gagctgatac cgctcgccgc agccgaacga ccgagcgcag cgagtcagtg   11700
agcgaggaag cggaagagcg cccaatacgc aaaccgcctc tccccgcgcg ttggccgatt   11760
ca                                                                  11762
```

<210> SEQ ID NO 8
<211> LENGTH: 38
<212> TYPE: DNA
<213> ORGANISM: artificial sequence
<220> FEATURE:
<223> OTHER INFORMATION: Primer

<400> SEQUENCE: 8
aactctctcc tctagagcat gtatataggt gatgagac          38

<210> SEQ ID NO 9
<211> LENGTH: 34
<212> TYPE: DNA
<213> ORGANISM: artificial sequence
<220> FEATURE:
<223> OTHER INFORMATION: Primer

<400> SEQUENCE: 9
gaattcttaa ttaatgtctg cattgcgcgt ctac             34

<210> SEQ ID NO 10
<211> LENGTH: 38
<212> TYPE: DNA
<213> ORGANISM: artificial sequence
<220> FEATURE:
<223> OTHER INFORMATION: Primer HTJP-662

<400> SEQUENCE: 10
agctggagct ccaccgcggc tttcaggcct tcgtaggc         38

<210> SEQ ID NO 11
<211> LENGTH: 35
<212> TYPE: DNA
<213> ORGANISM: artificial sequence
<220> FEATURE:
<223> OTHER INFORMATION: Primer HTJP-675

<400> SEQUENCE: 11
gtcatttagt ggatcccggc agatatccac tctag            35

<210> SEQ ID NO 12
<211> LENGTH: 43
<212> TYPE: DNA
<213> ORGANISM: artificial sequence
<220> FEATURE:
<223> OTHER INFORMATION: Primer HTJP-665

<400> SEQUENCE: 12
cctacaggag aattcttaat taaactccga gtacttgaga gtg    43

<210> SEQ ID NO 13
<211> LENGTH: 37
<212> TYPE: DNA
<213> ORGANISM: artificial sequence
<220> FEATURE:
<223> OTHER INFORMATION: Primer : HTJP-672

<400> SEQUENCE: 13
ctctctccag cggccgcggt tactgccctc ataccte          37

<210> SEQ ID NO 14
<211> LENGTH: 3491
<212> TYPE: DNA
<213> ORGANISM: Aspergillus niger

<400> SEQUENCE: 14
atgcggtggc ggctgcctgg cgcccggtcg acccttcctg ccagtgtcgc actcctcctg    60
ctccccgttc ttgttgctcc gcagcagtgg catgaacatc aacatgagct ctcctccacc   120
gtttccgtcc ctctccgacc gactggtttc acctccggcg tcgataccc tccctctttc    180 gacgtgaaat ccaacgatgc gagcgcccta gcaaccctgg ctctggccgg ctctggccgc   240

```
gccgttcgag cccctcctgc ccaagccagc agctctaccg ctggcctggc tccgcagctt    300
cacgcgcggt ccctgcagga ctgggaggtt gaggactttg tcctgctggc gaccgtcgac    360
ggttccattc acgcacgcga ccgcaagacc ggtgccgctc gttgggccct cgaggtcccg    420
agcagcccta tggtcgaaag cctctaccac cgagccaatc gctccagctt cgaccgtgcc    480
caaccagagg acgactttat ctggatcgtc gagccgagtc agggcggaag cctctacatc    540
tacagctcgg ggccagaggc aggcctccag aaattgggat tgactgtgaa ggaacttgtt    600
gacgaaacgc cttactcggg gactgacccg gccgttactt atacggcacg aaaggaaacg    660
acgctgtata ccatcgatgc tcgcaccgga acattctgc gggtgtttag ctctagaggt    720
cccatttcgt caggtcagga atgtcgaaag gttgatggtc tggatgtgga tatggaagaa    780
tgcgaatccc cttcgggtac tctagtcctt ggtcgtgtcg aatacacggt agccatccag    840
aacaccgaaa ccggtgatcc aatctgcact ctcaagtact cggagtggac ggccaacaac    900
cgggatatgg acctcagag ccagtacctc cgcacgatgg atcaaagcca tatttacagc    960
atgcatgatg gtgtagtctt aggcttcgat cattcacgga tggaccggcc acggtacacc   1020
cagcgattct cgagtccggt ggtccgcgtc ttcgatgttg ctcgtccggt cagcgccgac   1080
tcatctaacg accctactcc acttattcta ctctcgcagc ctctacagcc tcctgacccc   1140
gactacggta cgcttgacga tcgtgatgaa agagtattca ttgattacac cgagggtggt   1200
ggttggtatg ccatgtcgga ggccacctac ccgcttgtca ccgggagagc caagatggct   1260
caatgctacg aaaaagatta cctccgccat ggtcaacccc taacaagtct gaccccgagt   1320
cagcaacaag atgcactagc aggagtccat tctttgaacg gcccacgcgt cgtccgccgt   1380
cacatcccca gcatttctgg cccctcgtca gccgatatgt ccaatgacac gcctcgggag   1440
ttgatctata gctcatcgga cttggcactg cctccggctc tacgccacag caccattata   1500
cggaagggct gggacaatgc cattgatatt tttgtgacgc tcttgcttct gttttcggc   1560
accttcatct ggttcaattc tcatcacatt caggagcttg ctaagcagaa gctggatctg   1620
aaaaatatca tggcctcgta cggacagccg cccatgtcta cccctcaac tccaatcgtg   1680
gaagcccctc atttgaaacg cgaggctagc cctaatcgca tggcgaatct gactgtcgac   1740
atgaatgttt caggagagca gccgcagggt ggtgactcga cgccaaggcc caagaaatcc   1800
cagaactctc ttgcgcccga cacaactcca cgcgtacgca tccgggaacc gtctcaaggc   1860
ccagatggcg atgacgatgt ggacgagctc aatctacaag acggtgaaaa gcctaagaag   1920
aaggctcgcc gcgtcgtcg tggtggcaag aatcataggc ggggcaagaa gcccaatagc   1980
gacagcgaat ccagggaccc ggccgatcgc gttgttgatg aagtgaacaa gcttcaacct   2040
cagcctcgct tggaacccga tgtacagctg gcccggacgg tgtcgcatga gatcatggaa   2100
atggatggcg ttctccagat cggccgtctt agggtgttca ctgacgtggt cctgggacac   2160
ggcagccacg gaccgtggt gtatcggggc tcgttcgatg gacgcgacgt ggctgtcaag   2220
cgcatgctgg tagaattcta tgatattgca tcccatgaag tgggcctgtt gcaagaaagt   2280
gatgaccatg gcaatgtgat ccggtactac tgccgagagc aggctgctgg tttcctctac   2340
attgctttgg agctctgccc ggcctctttg caggatgtgg ttgaacgtcc atcagatttc   2400
ccgcagttag tccagggcgg cttggacctg ccggacgttc tgcgccagat tgtggcaggt   2460
gttcgctatc ttcattctct taagattgtg caccgcgatc tgaagccaca gaacatcttg   2520
gtggcgatgc ctcgcgggcg tactggttca cgctcccgc ggttgctgat ctcggatttc   2580
```

-continued

```
ggcttgtgta agaagctcga agacaaccag agctccttcc gcgcaactac ggcacatgcc    2640
gcgggtacct caggctggcg agccctgaa ttgctggtag acgacgacat gagcccggct    2700
atgcagggta gcgagtccca acacaccgaa tcatcagaac cagctgtggt ggatcctcaa    2760
accaaccggc gggctactcg agctatcgac atcttctctt tgggctgcgt cttttattac    2820
gttctgacgc gggggtgcca tccttttgac aagaatggca agtttatgcg cgaggccaac    2880
attgtcaagg caaccacaa cctcgatgag ctgcagcgtc tgggcgacta tgcctacgag    2940
gctgaagatc taatccagtc catgttgtcg cttgatcctc gacgacggta agtcgatgct    3000
cattacgtgc catgcatagt actaactttt ctagacccga tgcgagcgct gtgttgacgc    3060
acccgttctt ttggcctcca tctgaccgtc ttagcttcct ctgcgatgtc tcggatcact    3120
ttgaatttga accgcgggat cctccttcgg acgcccttt gtgtctcgag tcggtcgctc    3180
cacgagtgat gggcccggac atggatttcc tgcgactact gccacgggac tttaaggata    3240
atctcggcaa gcagcgtaag tacacgggat cgaagatgtt agatttgctg cgagccctcc    3300
ggaacaagcg caaccattac aacgacatgc cggagcatct caaggcacac atcggcgggt    3360
tgcccgaggg gtatcttaat ttttggactg tgcgattccc cagtcttctc atgagctgcc    3420
actccgtcat tgtggagttg cgtttgacgc ggtccgaccg tttcaagcgc tacttcacgg    3480
cgactgacta g                                                         3491
```

```
<210> SEQ ID NO 15
<211> LENGTH: 3444
<212> TYPE: DNA
<213> ORGANISM: Aspergillus niger
<220> FEATURE:
<221> NAME/KEY: CDS
<222> LOCATION: (1)..(3441)
<223> OTHER INFORMATION: Aspergillus niger wildtype IreA polypeptide

<400> SEQUENCE: 15
```

```
atg cgg tgg cgg ctg cct ggc gcc cgg tcg acc ctt cct gcc agt gtc     48
Met Arg Trp Arg Leu Pro Gly Ala Arg Ser Thr Leu Pro Ala Ser Val
1               5                   10                  15 gca ctc ctc ctg ctc ccc gtt ctt gtt gct ccg cag cag tgg cat gaa    96
Ala Leu Leu Leu Leu Pro Val Leu Val Ala Pro Gln Gln Trp His Glu
                20                  25                  30 cat caa cat gag ctc tcc tcc acc gtt tcc gtc cct ctc cga ccg act    144
His Gln His Glu Leu Ser Ser Thr Val Ser Val Pro Leu Arg Pro Thr
            35                  40                  45 ggt ttc acc tcc ggc gtc gat acc cct ccc tct ttc gac gtg aaa tcc    192
Gly Phe Thr Ser Gly Val Asp Thr Pro Pro Ser Phe Asp Val Lys Ser
        50                  55                  60 aac gat gcg agc gcc cta gca acc ctg gct ctg gcc ggc tct ggc cgc    240
Asn Asp Ala Ser Ala Leu Ala Thr Leu Ala Leu Ala Gly Ser Gly Arg
65                  70                  75                  80 gcc gtt cga gcc cct cct gcc caa gcc agc agc tct acc gct ggc ctg    288
Ala Val Arg Ala Pro Pro Ala Gln Ala Ser Ser Ser Thr Ala Gly Leu
                85                  90                  95 gct ccg cag ctt cac gcg cgg tcc ctg cag gac tgg gag gtt gag gac    336
Ala Pro Gln Leu His Ala Arg Ser Leu Gln Asp Trp Glu Val Glu Asp
                100                 105                 110 ttt gtc ctg ctg gcg acc gtc gac ggt tcc att cac gca cgc gac cgc    384
Phe Val Leu Leu Ala Thr Val Asp Gly Ser Ile His Ala Arg Asp Arg
            115                 120                 125 aag acc ggt gcc gct cgt tgg gcc ctc gag gtc ccg agc agc cct atg    432
Lys Thr Gly Ala Ala Arg Trp Ala Leu Glu Val Pro Ser Ser Pro Met
        130                 135                 140
```

-continued

| | |
|---|---|
| gtc gaa agc ctc tac cac cga gcc aat cgc tcc agc ttc gac cgt gcc<br>Val Glu Ser Leu Tyr His Arg Ala Asn Arg Ser Ser Phe Asp Arg Ala<br>145                    150                  155                  160 | 480 |
| caa cca gag gac gac ttt atc tgg atc gtc gag ccg agt cag ggc gga<br>Gln Pro Glu Asp Asp Phe Ile Trp Ile Val Glu Pro Ser Gln Gly Gly<br>                    165                  170                  175 | 528 |
| agc ctc tac atc tac agc tcg ggg cca gag gca ggc ctc cag aaa ttg<br>Ser Leu Tyr Ile Tyr Ser Ser Gly Pro Glu Ala Gly Leu Gln Lys Leu<br>                180                  185                  190 | 576 |
| gga ttg act gtg aag gaa ctt gtt gac gaa acg cct tac tcg ggg act<br>Gly Leu Thr Val Lys Glu Leu Val Asp Glu Thr Pro Tyr Ser Gly Thr<br>           195                  200                  205 | 624 |
| gac ccg gcc gtt act tat acg gca cga aag gaa acg acg ctg tat acc<br>Asp Pro Ala Val Thr Tyr Thr Ala Arg Lys Glu Thr Thr Leu Tyr Thr<br>210                    215                  220 | 672 |
| atc gat gct cgc acc gga aac att ctg cgg gtg ttt agc tct aga ggt<br>Ile Asp Ala Arg Thr Gly Asn Ile Leu Arg Val Phe Ser Ser Arg Gly<br>225                    230                  235                  240 | 720 |
| ccc att tcg tca ggt cag gaa tgt cga aag gtt gat ggt ctg gat gtg<br>Pro Ile Ser Ser Gly Gln Glu Cys Arg Lys Val Asp Gly Leu Asp Val<br>                    245                  250                  255 | 768 |
| gat atg gaa gaa tgc gaa tcc cct tcg ggt act cta gtc ctt ggt cgt<br>Asp Met Glu Glu Cys Glu Ser Pro Ser Gly Thr Leu Val Leu Gly Arg<br>                260                  265                  270 | 816 |
| gtc gaa tac acg gta gcc atc cag aac acc gaa acc ggt gat cca atc<br>Val Glu Tyr Thr Val Ala Ile Gln Asn Thr Glu Thr Gly Asp Pro Ile<br>           275                  280                  285 | 864 |
| tgc act ctc aag tac tcg gag tgg acg gcc aac aac cgg gat atg gac<br>Cys Thr Leu Lys Tyr Ser Glu Trp Thr Ala Asn Asn Arg Asp Met Asp<br>290                    295                  300 | 912 |
| ctc cag agc cag tac ctc cgc acg atg gat caa agc cat att tac agc<br>Leu Gln Ser Gln Tyr Leu Arg Thr Met Asp Gln Ser His Ile Tyr Ser<br>305                    310                  315                  320 | 960 |
| atg cat gat ggt gta gtc tta ggc ttc gat cat tca cgg atg gac cgg<br>Met His Asp Gly Val Leu Gly Phe Asp His Ser Arg Met Asp Arg<br>                    325                  330                  335 | 1008 |
| cca cgg tac acc cag cga ttc tcg agt ccg gtg gtc cgc gtc ttc gat<br>Pro Arg Tyr Thr Gln Arg Phe Ser Ser Pro Val Val Arg Val Phe Asp<br>                340                  345                  350 | 1056 |
| gtt gct cgt ccg gtc agc gcc gac tca tct aac gac cct act cca ctt<br>Val Ala Arg Pro Val Ser Ala Asp Ser Ser Asn Asp Pro Thr Pro Leu<br>           355                  360                  365 | 1104 |
| att cta ctc tcg cag cct cta cag cct cct gac ccc gac tac ggt acg<br>Ile Leu Leu Ser Gln Pro Leu Gln Pro Pro Asp Pro Asp Tyr Gly Thr<br>370                    375                  380 | 1152 |
| ctt gac gat cgt gat gaa aga gta ttc att gat tac acc gag ggt ggt<br>Leu Asp Asp Arg Asp Glu Arg Val Phe Ile Asp Tyr Thr Glu Gly Gly<br>385                    390                  395                  400 | 1200 |
| ggt tgg tat gcc atg tcg gag gcc acc tac ccg ctt gtc acc ggg aga<br>Gly Trp Tyr Ala Met Ser Glu Ala Thr Tyr Pro Leu Val Thr Gly Arg<br>                    405                  410                  415 | 1248 |
| gcc aag atg gct caa tgc tac gaa aaa gat tac ctc cgc cat ggt caa<br>Ala Lys Met Ala Gln Cys Tyr Glu Lys Asp Tyr Leu Arg His Gly Gln<br>                420                  425                  430 | 1296 |
| ccc cta aca agt ctg acc ccg agt cag caa caa gat gca cta gca gga<br>Pro Leu Thr Ser Leu Thr Pro Ser Gln Gln Gln Asp Ala Leu Ala Gly<br>           435                  440                  445 | 1344 |
| gtc cat tct ttg aac ggc cca cgc gtc gtc cgc cgt cac atc ccc agc<br>Val His Ser Leu Asn Gly Pro Arg Val Val Arg Arg His Ile Pro Ser | 1392 |

-continued

```
            450                 455                 460
att tct ggc ccc tcg tca gcc gat atg tcc aat gac acg cct cgg gag    1440
Ile Ser Gly Pro Ser Ser Ala Asp Met Ser Asn Asp Thr Pro Arg Glu
465                 470                 475                 480 ttg atc tat agc tca tcg gac ttg gca ctg cct ccg gct cta cgc cac    1488
Leu Ile Tyr Ser Ser Ser Asp Leu Ala Leu Pro Pro Ala Leu Arg His
                485                 490                 495 agc acc att ata cgg aag ggc tgg gac aat gcc att gat att ttt gtg    1536
Ser Thr Ile Ile Arg Lys Gly Trp Asp Asn Ala Ile Asp Ile Phe Val
            500                 505                 510 acg ctc ttg ctt ctg ttt ttc ggc acc ttc atc tgg ttc aat tct cat    1584
Thr Leu Leu Leu Leu Phe Phe Gly Thr Phe Ile Trp Phe Asn Ser His
            515                 520                 525 cac att cag gag ctt gct aag cag aag ctg gat ctg aaa aat atc atg    1632
His Ile Gln Glu Leu Ala Lys Gln Lys Leu Asp Leu Lys Asn Ile Met
            530                 535                 540 gcc tcg tac gga cag ccg ccc atg tct acc ccc tca act cca atc gtg    1680
Ala Ser Tyr Gly Gln Pro Pro Met Ser Thr Pro Ser Thr Pro Ile Val
545                 550                 555                 560 gaa gcc cct cat ttg aaa cgc gag gct agc cct aat cgc atg gcg aat    1728
Glu Ala Pro His Leu Lys Arg Glu Ala Ser Pro Asn Arg Met Ala Asn
                565                 570                 575 ctg act gtc gac atg aat gtt tca gga gag cag ccg cag ggt ggt gac    1776
Leu Thr Val Asp Met Asn Val Ser Gly Glu Gln Pro Gln Gly Gly Asp
            580                 585                 590 tcg acg cca agg ccc aag aaa tcc cag aac tct ctt gcg ccc gac aca    1824
Ser Thr Pro Arg Pro Lys Lys Ser Gln Asn Ser Leu Ala Pro Asp Thr
            595                 600                 605 act cca cgc gta cgc atc cgg gaa ccg tct caa ggc cca gat ggc gat    1872
Thr Pro Arg Val Arg Ile Arg Glu Pro Ser Gln Gly Pro Asp Gly Asp
610                 615                 620 gac gat gtg gac gag ctc aat cta caa gac ggt gaa aag cct aag aag    1920
Asp Asp Val Asp Glu Leu Asn Leu Gln Asp Gly Glu Lys Pro Lys Lys
625                 630                 635                 640 aag gct cgc cgc ggt cgt cgt ggt ggc aag aat cat agg cgg ggc aag    1968
Lys Ala Arg Arg Gly Arg Arg Gly Gly Lys Asn His Arg Arg Gly Lys
                645                 650                 655 aag ccc aat agc gac agc gaa tcc agg gac ccg gcc gat cgc gtt gtt    2016
Lys Pro Asn Ser Asp Ser Glu Ser Arg Asp Pro Ala Asp Arg Val Val
            660                 665                 670 gat gaa gtg aac aag ctt caa cct cag cct cgc ttg gaa ccc gat gta    2064
Asp Glu Val Asn Lys Leu Gln Pro Gln Pro Arg Leu Glu Pro Asp Val
            675                 680                 685 cag ctg gcc cgg acg gtg tcg cat gag atc atg gaa atg gat ggc gtt    2112
Gln Leu Ala Arg Thr Val Ser His Glu Ile Met Glu Met Asp Gly Val
690                 695                 700 ctc cag atc ggc cgt ctt agg gtg ttc act gac gtg gtc ctg gga cac    2160
Leu Gln Ile Gly Arg Leu Arg Val Phe Thr Asp Val Val Leu Gly His
705                 710                 715                 720 ggc agc cac ggg acc gtg gtg tat cgg ggc tcg ttc gat gga cgc gac    2208
Gly Ser His Gly Thr Val Val Tyr Arg Gly Ser Phe Asp Gly Arg Asp
                725                 730                 735 gtg gct gtc aag cgc atg ctg gta gaa ttc tat gat att gca tcc cat    2256
Val Ala Val Lys Arg Met Leu Val Glu Phe Tyr Asp Ile Ala Ser His
                740                 745                 750 gaa gtg ggc ctg ttg caa gaa agt gat gac cat ggc aat gtg atc cgg    2304
Glu Val Gly Leu Leu Gln Glu Ser Asp Asp His Gly Asn Val Ile Arg
            755                 760                 765 tac tac tgc cga gag cag gct gct ggt ttc ctc tac att gct ttg gag    2352
```

```
            Tyr Tyr Cys Arg Glu Gln Ala Ala Gly Phe Leu Tyr Ile Ala Leu Glu
                770             775                 780 ctc tgc ccg gcc tct ttg cag gat gtg gtt gaa cgt cca tca gat ttc         2400
Leu Cys Pro Ala Ser Leu Gln Asp Val Val Glu Arg Pro Ser Asp Phe
785                 790                 795                 800 ccg cag tta gtc cag ggc ggc ttg gac ctg ccg gac gtt ctg cgc cag         2448
Pro Gln Leu Val Gln Gly Gly Leu Asp Leu Pro Asp Val Leu Arg Gln
                805                 810                 815 att gtg gca ggt gtt cgc tat ctt cat tct ctt aag att gtg cac cgc         2496
Ile Val Ala Gly Val Arg Tyr Leu His Ser Leu Lys Ile Val His Arg
            820                 825                 830 gat ctg aag cca cag aac atc ttg gtg gcg atg cct cgc ggg cgt act         2544
Asp Leu Lys Pro Gln Asn Ile Leu Val Ala Met Pro Arg Gly Arg Thr
                835                 840                 845 ggt tca cgc tcc ctg cgg ttg ctg atc tcg gat ttc ggc ttg tgt aag         2592
Gly Ser Arg Ser Leu Arg Leu Leu Ile Ser Asp Phe Gly Leu Cys Lys
850                 855                 860 aag ctc gaa gac aac cag agc tcc ttc cgc gca act acg gca cat gcc         2640
Lys Leu Glu Asp Asn Gln Ser Ser Phe Arg Ala Thr Thr Ala His Ala
865                 870                 875                 880 gcg ggt acc tca ggc tgg cga gcc cct gaa ttg ctg gta gac gac gac         2688
Ala Gly Thr Ser Gly Trp Arg Ala Pro Glu Leu Leu Val Asp Asp Asp
                885                 890                 895 atg agc ccg gct atg cag ggt agc gag tcc caa cac acc gaa tca tca         2736
Met Ser Pro Ala Met Gln Gly Ser Glu Ser Gln His Thr Glu Ser Ser
                900                 905                 910 gaa cca gct gtg gtg gat cct caa acc aac cgg cgg gct act cga gct         2784
Glu Pro Ala Val Val Asp Pro Gln Thr Asn Arg Arg Ala Thr Arg Ala
            915                 920                 925 atc gac atc ttc tct ttg ggc tgc gtc ttt tat tac gtt ctg acg cgg         2832
Ile Asp Ile Phe Ser Leu Gly Cys Val Phe Tyr Tyr Val Leu Thr Arg
930                 935                 940 ggg tgc cat cct ttt gac aag aat ggc aag ttt atg cgc gag gcc aac         2880
Gly Cys His Pro Phe Asp Lys Asn Gly Lys Phe Met Arg Glu Ala Asn
945                 950                 955                 960 att gtc aag ggc aac cac aac ctc gat gag ctg cag cgt ctg ggc gac         2928
Ile Val Lys Gly Asn His Asn Leu Asp Glu Leu Gln Arg Leu Gly Asp
                965                 970                 975 tat gcc tac gag gct gaa gat cta atc cag tcc atg ttg tcg ctt gat         2976
Tyr Ala Tyr Glu Ala Glu Asp Leu Ile Gln Ser Met Leu Ser Leu Asp
            980                 985                 990 cct cga cga cga ccc gat gcg agc gct gtg ttg acg cac ccg ttc ttt         3024
Pro Arg Arg Arg Pro Asp Ala Ser Ala Val Leu Thr His Pro Phe Phe
                995                 1000                1005 tgg cct cca tct gac cgt ctt agc ttc ctc tgc gat gtc tcg gat             3069
Trp Pro Pro Ser Asp Arg Leu Ser Phe Leu Cys Asp Val Ser Asp
    1010                1015                1020 cac ttt gaa ttt gaa ccg cgg gat cct cct tcg gac gcc ctt ttg             3114
His Phe Glu Phe Glu Pro Arg Asp Pro Pro Ser Asp Ala Leu Leu
    1025                1030                1035 tgt ctc gag tcg gtc gct cca cga gtg atg ggc ccg gac atg gat             3159
Cys Leu Glu Ser Val Ala Pro Arg Val Met Gly Pro Asp Met Asp
    1040                1045                1050 ttc ctg cga cta ctg cca cgg gac ttt aag gat aat ctc ggc aag             3204
Phe Leu Arg Leu Leu Pro Arg Asp Phe Lys Asp Asn Leu Gly Lys
    1055                1060                1065 cag cgt aag tac acg gga tcg aag atg tta gat ttg ctg cga gcc             3249
Gln Arg Lys Tyr Thr Gly Ser Lys Met Leu Asp Leu Leu Arg Ala
    1070                1075                1080
```

-continued

| | |
|---|---|
| ctc cgg aac aag cgc aac cat tac aac gac atg ccg gag cat ctc<br>Leu Arg Asn Lys Arg Asn His Tyr Asn Asp Met Pro Glu His Leu<br>1085                    1090                    1095 | 3294 |
| aag gca cac atc ggc ggg ttg ccc gag ggg tat ctt aat ttt tgg<br>Lys Ala His Ile Gly Gly Leu Pro Glu Gly Tyr Leu Asn Phe Trp<br>1100                    1105                    1110 | 3339 |
| act gtg cga ttc ccc agt ctt ctc atg agc tgc cac tcc gtc att<br>Thr Val Arg Phe Pro Ser Leu Leu Met Ser Cys His Ser Val Ile<br>1115                    1120                    1125 | 3384 |
| gtg gag ttg cgt ttg acg cgg tcc gac cgt ttc aag cgc tac ttc<br>Val Glu Leu Arg Leu Thr Arg Ser Asp Arg Phe Lys Arg Tyr Phe<br>1130                    1135                    1140 | 3429 |
| acg gcg act gac tag<br>Thr Ala Thr Asp<br>1145 | 3444 |

<210> SEQ ID NO 16
<211> LENGTH: 1147
<212> TYPE: PRT
<213> ORGANISM: Aspergillus niger

<400> SEQUENCE: 16

Met Arg Trp Arg Leu Pro Gly Ala Arg Ser Thr Leu Pro Ala Ser Val
1               5                   10                  15

Ala Leu Leu Leu Pro Val Leu Val Ala Pro Gln Gln Trp His Glu
            20                  25                  30

His Gln His Glu Leu Ser Ser Thr Val Ser Val Pro Leu Arg Pro Thr
        35                  40                  45

Gly Phe Thr Ser Gly Val Asp Thr Pro Pro Ser Phe Asp Val Lys Ser
    50                  55                  60

Asn Asp Ala Ser Ala Leu Ala Thr Leu Ala Leu Ala Gly Ser Gly Arg
65                  70                  75                  80

Ala Val Arg Ala Pro Pro Ala Gln Ala Ser Ser Ser Thr Ala Gly Leu
                85                  90                  95

Ala Pro Gln Leu His Ala Arg Ser Leu Gln Asp Trp Glu Val Glu Asp
            100                 105                 110

Phe Val Leu Leu Ala Thr Val Asp Gly Ser Ile His Ala Arg Asp Arg
        115                 120                 125

Lys Thr Gly Ala Ala Arg Trp Ala Leu Glu Val Pro Ser Ser Pro Met
    130                 135                 140

Val Glu Ser Leu Tyr His Arg Ala Asn Arg Ser Ser Phe Asp Arg Ala
145                 150                 155                 160

Gln Pro Glu Asp Asp Phe Ile Trp Ile Val Glu Pro Ser Gln Gly Gly
                165                 170                 175

Ser Leu Tyr Ile Tyr Ser Ser Gly Pro Glu Ala Gly Leu Gln Lys Leu
            180                 185                 190

Gly Leu Thr Val Lys Glu Leu Val Asp Glu Thr Pro Tyr Ser Gly Thr
        195                 200                 205

Asp Pro Ala Val Thr Tyr Thr Ala Arg Lys Glu Thr Thr Leu Tyr Thr
    210                 215                 220

Ile Asp Ala Arg Thr Gly Asn Ile Leu Arg Val Phe Ser Ser Arg Gly
225                 230                 235                 240

Pro Ile Ser Ser Gly Gln Glu Cys Arg Lys Val Asp Gly Leu Asp Val
                245                 250                 255

Asp Met Glu Glu Cys Gly Ser Pro Ser Gly Thr Leu Val Leu Gly Arg
            260                 265                 270

```
Val Glu Tyr Thr Val Ala Ile Gln Asn Thr Glu Thr Gly Asp Pro Ile
            275                 280                 285

Cys Thr Leu Lys Tyr Ser Glu Trp Thr Ala Asn Asn Arg Asp Met Asp
            290                 295                 300

Leu Gln Ser Gln Tyr Leu Arg Thr Met Asp Gln Ser His Ile Tyr Ser
305                 310                 315                 320

Met His Asp Gly Val Val Leu Gly Phe Asp His Ser Arg Met Asp Arg
                325                 330                 335

Pro Arg Tyr Thr Gln Arg Phe Ser Pro Val Val Arg Val Phe Asp
            340                 345                 350

Val Ala Arg Pro Val Ser Ala Asp Ser Ser Asn Asp Pro Thr Pro Leu
            355                 360                 365

Ile Leu Leu Ser Gln Pro Leu Gln Pro Pro Asp Pro Asp Tyr Gly Thr
            370                 375                 380

Leu Asp Asp Arg Asp Glu Arg Val Phe Ile Asp Tyr Thr Glu Gly Gly
385                 390                 395                 400

Gly Trp Tyr Ala Met Ser Glu Ala Thr Tyr Pro Leu Val Thr Gly Arg
                405                 410                 415

Ala Lys Met Ala Gln Cys Tyr Glu Lys Asp Tyr Leu Arg His Gly Gln
                420                 425                 430

Pro Leu Thr Ser Leu Thr Pro Ser Gln Gln Gln Asp Ala Leu Ala Gly
            435                 440                 445

Val His Ser Leu Asn Gly Pro Arg Val Val Arg His Ile Pro Ser
            450                 455                 460

Ile Ser Gly Pro Ser Ser Ala Asp Met Ser Asn Asp Thr Pro Arg Glu
465                 470                 475                 480

Leu Ile Tyr Ser Ser Ser Asp Leu Ala Leu Pro Pro Ala Leu Arg His
                485                 490                 495

Ser Thr Ile Ile Arg Lys Gly Trp Asp Asn Ala Ile Asp Ile Phe Val
            500                 505                 510

Thr Leu Leu Leu Leu Phe Phe Gly Thr Phe Ile Trp Phe Asn Ser His
            515                 520                 525

His Ile Gln Glu Leu Ala Lys Gln Lys Leu Asp Leu Lys Asn Ile Met
            530                 535                 540

Ala Ser Tyr Gly Gln Pro Pro Met Ser Thr Pro Ser Thr Pro Ile Val
545                 550                 555                 560

Glu Ala Pro His Leu Lys Arg Glu Ala Ser Pro Asn Arg Met Ala Asn
                565                 570                 575

Leu Thr Val Asp Met Asn Val Ser Gly Glu Gln Pro Gln Gly Gly Asp
            580                 585                 590

Ser Thr Pro Arg Pro Lys Lys Ser Gln Asn Ser Leu Ala Pro Asp Thr
            595                 600                 605

Thr Pro Arg Val Arg Ile Arg Glu Pro Ser Gln Gly Pro Asp Gly Asp
            610                 615                 620

Asp Asp Val Asp Glu Leu Asn Leu Gln Asp Gly Glu Lys Pro Lys Lys
625                 630                 635                 640

Lys Ala Arg Arg Gly Arg Arg Gly Gly Lys Asn His Arg Arg Gly Lys
                645                 650                 655

Lys Pro Asn Ser Asp Ser Glu Ser Arg Asp Pro Ala Asp Arg Val Val
                660                 665                 670

Asp Glu Val Asn Lys Leu Gln Pro Gln Pro Arg Leu Glu Pro Asp Val
            675                 680                 685

Gln Leu Ala Arg Thr Val Ser His Glu Ile Met Glu Met Asp Gly Val
```

```
              690             695             700
Leu Gln Ile Gly Arg Leu Arg Val Phe Thr Asp Val Val Leu Gly His
705                     710                 715                 720

Gly Ser His Gly Thr Val Val Tyr Arg Gly Ser Phe Asp Gly Arg Asp
            725                 730                 735

Val Ala Val Lys Arg Met Leu Val Glu Phe Tyr Asp Ile Ala Ser His
        740                 745                 750

Glu Val Gly Leu Leu Gln Glu Ser Asp Asp His Gly Asn Val Ile Arg
    755                 760                 765

Tyr Tyr Cys Arg Glu Gln Ala Ala Gly Phe Leu Tyr Ile Ala Leu Glu
770                 775                 780

Leu Cys Pro Ala Ser Leu Gln Asp Val Val Glu Arg Pro Ser Asp Phe
785                 790                 795                 800

Pro Gln Leu Val Gln Gly Gly Leu Asp Leu Pro Asp Val Leu Arg Gln
                805                 810                 815

Ile Val Ala Gly Val Arg Tyr Leu His Ser Leu Lys Ile Val His Arg
            820                 825                 830

Asp Leu Lys Pro Gln Asn Ile Leu Val Ala Met Pro Arg Gly Arg Thr
        835                 840                 845

Gly Ser Arg Ser Leu Arg Leu Leu Ile Ser Asp Phe Gly Leu Cys Lys
    850                 855                 860

Lys Leu Glu Asp Asn Gln Ser Ser Phe Arg Ala Thr Thr Ala His Ala
865                 870                 875                 880

Ala Gly Thr Ser Gly Trp Arg Ala Pro Glu Leu Leu Val Asp Asp Asp
                885                 890                 895

Met Ser Pro Ala Met Gln Gly Ser Glu Ser Gln His Thr Glu Ser Ser
            900                 905                 910

Glu Pro Ala Val Val Asp Pro Gln Thr Asn Arg Arg Ala Thr Arg Ala
        915                 920                 925

Ile Asp Ile Phe Ser Leu Gly Cys Val Phe Tyr Tyr Val Leu Thr Arg
    930                 935                 940

Gly Cys His Pro Phe Asp Lys Asn Gly Lys Phe Met Arg Glu Ala Asn
945                 950                 955                 960

Ile Val Lys Gly Asn His Asn Leu Asp Glu Leu Gln Arg Leu Gly Asp
                965                 970                 975

Tyr Ala Tyr Glu Ala Glu Asp Leu Ile Gln Ser Met Leu Ser Leu Asp
            980                 985                 990

Pro Arg Arg Arg Pro Asp Ala Ser Ala Val Leu Thr His Pro Phe Phe
        995                 1000                1005

Trp Pro Pro Ser Asp Arg Leu Ser Phe Leu Cys Asp Val Ser Asp
    1010                1015                1020

His Phe Glu Phe Glu Pro Arg Asp Pro Pro Ser Asp Ala Leu Leu
    1025                1030                1035

Cys Leu Glu Ser Val Ala Pro Arg Val Met Gly Pro Asp Met Asp
    1040                1045                1050

Phe Leu Arg Leu Leu Pro Arg Asp Phe Lys Asp Asn Leu Gly Lys
    1055                1060                1065

Gln Arg Lys Tyr Thr Gly Ser Lys Met Leu Asp Leu Leu Arg Ala
    1070                1075                1080

Leu Arg Asn Lys Arg Asn His Tyr Asn Asp Met Pro Glu His Leu
    1085                1090                1095

Lys Ala His Ile Gly Gly Leu Pro Glu Gly Tyr Leu Asn Phe Trp
    1100                1105                1110
```

```
Thr Val Arg Phe Pro Ser Leu Leu Met Ser Cys His Ser Val Ile
    1115                1120                1125

Val Glu Leu Arg Leu Thr Arg Ser Asp Arg Phe Lys Arg Tyr Phe
    1130                1135                1140

Thr Ala Thr Asp
    1145

<210> SEQ ID NO 17
<211> LENGTH: 3491
<212> TYPE: DNA
<213> ORGANISM: artificial sequence
<220> FEATURE:
<223> OTHER INFORMATION: Genomic DNA sequence of a mutated Aspergillus
      niger ireA-gene of the invention.

<400> SEQUENCE: 17
```

| | | | | | |
|---|---|---|---|---|---|
| atgcggtggc | ggctgcctgg | cgcccggtcg | acccttcctg | ccagtgtcgc | actcctcctg | 60 |
| ctccccgttc | ttgttgctcc | gcagcagtgg | catgaacatc | aacatgagct | cctcctccacc | 120 |
| gtttccgtcc | ctctccgacc | gactggtttc | acctccggcg | tcgataccc | tccctctttc | 180 |
| gacgtgaaat | ccaacgatgc | gagcgcccta | gcaaccctgg | ctctggccgg | ctctggccgc | 240 |
| accgttcgaa | cccctcctgc | ccaagccagc | agctctaccg | ctggcctggc | tccgcagctt | 300 |
| cacgcgcggt | ccctgcagga | ctgggaggtt | gaggactttg | tcctgctggc | gaccgtcgac | 360 |
| ggttccattc | acgcacgcga | ccgcaagacc | ggtgccgctc | gttgggccct | cgaggtcccg | 420 |
| agcagcccta | tggtcgaaag | cctctaccac | cgagccaatc | gctccagctt | cgaccgtgcc | 480 |
| caaccagagg | acgactttat | ctggatcgtc | gagccgagtc | agggcggaag | cctctacatc | 540 |
| tacagctcgg | ggccagaggc | aggcctccag | aaattgggat | tgactgtgaa | ggaacttgtt | 600 |
| gacgaaacgc | cttactcggg | gactgacccg | gccgttactt | atacggcacg | aaaggaaacg | 660 |
| acgctgtata | ccatcgatgc | tcgcaccgga | aacattctgc | gggtgtttag | ctctagaggt | 720 |
| cccatttcgt | caggtcagga | atgtcgaaag | gttgatggtc | tggatgtgga | tatggaagaa | 780 |
| tgcgaatccc | cttcgggtac | tctagtcctt | ggtcgtgtcg | aatacacggt | agccatccag | 840 |
| aacaccgaaa | ccggtgatcc | aatctgcact | ctcaagtact | cggagtggac | ggccaacaac | 900 |
| cgggatatgg | acctccagag | ccagtacctc | cgcacgatgg | atcaaagcca | tatttacagc | 960 |
| atgcatgatg | gtgtagtctt | aggcttcgat | cattcacgga | tggaccggcc | acggtacacc | 1020 |
| cagcgattct | cgagtccggt | ggtccgcgtc | ttcgatgttg | ctcgtccggt | cagcgccgac | 1080 |
| tcatctaacg | accctactcc | acttattcta | ctctcgcagc | ctctacagcc | tcctgacccc | 1140 |
| gactacggta | cgcttgacga | tcgtgatgaa | agagtattca | ttgattacac | cgagggtggt | 1200 |
| ggttggtatg | ccatgtcgga | ggccacctac | ccgcttgtca | ccgggagagc | caagatggct | 1260 |
| caatgctacg | aaaaagatta | cctccgccat | ggtcaacccc | taacaagtct | gaccccgagt | 1320 |
| cagcaacaag | atgcactagc | aggagtccat | tctttgaacg | gccacgcgt | cgtccgccgt | 1380 |
| cacatcccca | gcatttctgg | ccccctcgtca | gccgatatgt | ccaatgacac | gcctcgggag | 1440 |
| ttgatctata | gctcatcgga | cttggcactg | cctccggctc | tacgccacag | caccattata | 1500 |
| cggaagggct | gggacaatgc | cattgatatt | tttgtgacgc | tcttgcttct | gtttttcggc | 1560 |
| accttcatct | ggttcaattc | tcatcacatt | caggagcttg | ctaagcagaa | gctggatctg | 1620 |
| aaaaatatca | tggcctcgta | cggacagccg | cccatgtcta | ccccctcaac | tccaatcgtg | 1680 |
| gaagcccctc | atttgaaacg | cgaggctagc | cctaatcgca | tggcgaatct | gactgtcgac | 1740 |

```
atgaatgttt caggagagca gccgcagggt ggtgactcga cgccaaggcc caagaaatcc    1800
cagaactctc ttgcgcccga cacaactcca cgcgtacgca tccgggaacc gtctcaaggc    1860
ccagatggcg atgacgatgt ggacgagctc aatctacaag acggtgaaaa gcctaagaag    1920
aaggctcgcc gcggtcgtcg tggtggcaag aatcataggc ggggcaagaa gcccaatagc    1980
gacagcgaat ccagggaccc ggccgatcgc gttgttgatg aagtgaacaa gcttcaacct    2040
cagcctcgct tggaacccga tgtacagctg gcccggacgg tgtcgcatga gatcatggaa    2100
atggatggcg ttctccagat cggccgtctt agggtgttca ctgacgtggt cctgggacac    2160
ggcagccacg ggaccgtggt gtatcggggc tcgttcgatg gacgcgacgt ggctgtcaag    2220
cgcatgctgg tagaattcta tgatattgca tcccatgaag tgggcctgtt gcaagaaagt    2280
gatgaccatg gcaatgtgat ccggtactac tgccgagagc aggctgctgg tttcctctac    2340
attgctttgg agctctgccc ggcctctttg caggatgtgg ttgaacgtcc atcagatttc    2400
ccgcagttag tccagggcgg cttggacctg ccggacgttc tgcgccagat tgtggcaggt    2460
gttcgctatc ttcattctct taagattgtg caccgcgatc tgaagccaca gaacatcttg    2520
gtggcgatgc ctcgcgggcg tactggttca cgctccctgc ggttgctgat ctcggatttc    2580
ggcttgtgta agaagctcga agacaaccag agctccttcc gcgcaactac ggcacatgcc    2640
gcgggtacct caggctggcg agcccctgaa ttgctggtag acgacgacat gagcccggct    2700
atgcagggta gcgagtccca acacaccgaa tcatcagaac cagctgtggt ggatcctcaa    2760
accaaccggc gggctactcg agctatcgac atcttctctt gggctgcgt cttttattac    2820
gttctgacgc ggggtgcca tccttttgac aagaatggca agtttatgcg cgaggccaac    2880
attgtcaagg gcaaccacaa cctcgatgag ctgcagcgtc tgggcgacta tgcctacgag    2940
gctgaagatc taatccagtc catgttgtcg cttgatcctc gacgacggta agtcgatgct    3000
cattacgtgc catgcatagt actaactttt ctagacccga tgcgagcgct gtgttgacgc    3060
acccgttctt ttggcctcca tctgaccgtc ttagcttcct ctgcgatgtc tcggatcact    3120
ttgaatttga accgcgggat cctccttcgg acgccctttt gtgtctcgag tcggtcgctc    3180
cacgagtgat gggcccggac atggatttcc tgcgactact gccacgggac tttaaggata    3240
atctcggcaa gcagcgtaag tacacgggat cgaagatgtt agatttgctg cgagccctcc    3300
ggaacaagcg caaccattac aacgacatgc cggagcatct caaggcacac atcgcgggt    3360
tgcccgaggg gtatcttaat ttttggactg tgcgattccc cagtcttctc atgagctgcc    3420
actccgtcat tgtggagttg cgtttgacgc ggtccgaccg tttcaagcgc tacttcacgg    3480
cgactgacta g                                                        3491
```

<210> SEQ ID NO 18
<211> LENGTH: 3444
<212> TYPE: DNA
<213> ORGANISM: artificial sequence
<220> FEATURE:
<223> OTHER INFORMATION: cDNA sequence of a mutated Aspergillus niger
      ireA-gene of the invention.
<220> FEATURE:
<221> NAME/KEY: CDS
<222> LOCATION: (1)..(3441)
<223> OTHER INFORMATION: Modified Aspergillus niger IreA polypeptide
      according to the invention.

<400> SEQUENCE: 18

```
atg cgg tgg cgg ctg cct ggc gcc cgg tcg acc ctt cct gcc agt gtc      48
Met Arg Trp Arg Leu Pro Gly Ala Arg Ser Thr Leu Pro Ala Ser Val
1               5                   10                  15
```

-continued

```
gca ctc ctc ctg ctc ccc gtt ctt gtt gct ccg cag cag tgg cat gaa      96
Ala Leu Leu Leu Leu Pro Val Leu Val Ala Pro Gln Gln Trp His Glu
         20                  25                  30 cat caa cat gag ctc tcc tcc acc gtt tcc gtc cct ctc cga ccg act     144
His Gln His Glu Leu Ser Ser Thr Val Ser Val Pro Leu Arg Pro Thr
     35                  40                  45 ggt ttc acc tcc ggc gtc gat acc cct ccc tct ttc gac gtg aaa tcc     192
Gly Phe Thr Ser Gly Val Asp Thr Pro Pro Ser Phe Asp Val Lys Ser
 50                  55                  60 aac gat gcg agc gcc cta gca acc ctg gct ctg gcc ggc tct ggc cgc     240
Asn Asp Ala Ser Ala Leu Ala Thr Leu Ala Leu Ala Gly Ser Gly Arg
 65                  70                  75                  80 acc gtt cga acc cct cct gcc caa gcc agc agc tct acc gct ggc ctg     288
Thr Val Arg Thr Pro Pro Ala Gln Ala Ser Ser Ser Thr Ala Gly Leu
                 85                  90                  95 gct ccg cag ctt cac gcg cgg tcc ctg cag gac tgg gag gtt gag gac     336
Ala Pro Gln Leu His Ala Arg Ser Leu Gln Asp Trp Glu Val Glu Asp
             100                 105                 110 ttt gtc ctg ctg gcg acc gtc gac ggt tcc att cac gca cgc gac cgc     384
Phe Val Leu Leu Ala Thr Val Asp Gly Ser Ile His Ala Arg Asp Arg
         115                 120                 125 aag acc ggt gcc gct cgt tgg gcc ctc gag gtc ccg agc agc cct atg     432
Lys Thr Gly Ala Ala Arg Trp Ala Leu Glu Val Pro Ser Ser Pro Met
130                 135                 140 gtc gaa agc ctc tac cac cga gcc aat cgc tcc agc ttc gac cgt gcc     480
Val Glu Ser Leu Tyr His Arg Ala Asn Arg Ser Ser Phe Asp Arg Ala
145                 150                 155                 160 caa cca gag gac gac ttt atc tgg atc gtc gag ccg agt cag ggc gga     528
Gln Pro Glu Asp Asp Phe Ile Trp Ile Val Glu Pro Ser Gln Gly Gly
                 165                 170                 175 agc ctc tac atc tac agc tcg ggg cca gag gca ggc ctc cag aaa ttg     576
Ser Leu Tyr Ile Tyr Ser Ser Gly Pro Glu Ala Gly Leu Gln Lys Leu
             180                 185                 190 gga ttg act gtg aag gaa ctt gtt gac gaa acg cct tac tcg ggg act     624
Gly Leu Thr Val Lys Glu Leu Val Asp Glu Thr Pro Tyr Ser Gly Thr
         195                 200                 205 gac ccg gcc gtt act tat acg gca cga aag gaa acg acg ctg tat acc     672
Asp Pro Ala Val Thr Tyr Thr Ala Arg Lys Glu Thr Thr Leu Tyr Thr
210                 215                 220 atc gat gct cgc acc gga aac att ctg cgg gtg ttt agc tct aga ggt     720
Ile Asp Ala Arg Thr Gly Asn Ile Leu Arg Val Phe Ser Ser Arg Gly
225                 230                 235                 240 ccc att tcg tca ggt cag gaa tgt cga aag gtt gat ggt ctg gat gtg     768
Pro Ile Ser Ser Gly Gln Glu Cys Arg Lys Val Asp Gly Leu Asp Val
                 245                 250                 255 gat atg gaa gaa tgc gaa tcc cct tcg ggt act cta gtc ctt ggt cgt     816
Asp Met Glu Glu Cys Glu Ser Pro Ser Gly Thr Leu Val Leu Gly Arg
             260                 265                 270 gtc gaa tac acg gta gcc atc cag aac acc gaa acc ggt gat cca atc     864
Val Glu Tyr Thr Val Ala Ile Gln Asn Thr Glu Thr Gly Asp Pro Ile
         275                 280                 285 tgc act ctc aag tac tcg gag tgg acg gcc aac aac cgg gat atg gac     912
Cys Thr Leu Lys Tyr Ser Glu Trp Thr Ala Asn Asn Arg Asp Met Asp
290                 295                 300 ctc cag agc cag tac ctc cgc acg atg gat caa agc cat att tac agc     960
Leu Gln Ser Gln Tyr Leu Arg Thr Met Asp Gln Ser His Ile Tyr Ser
305                 310                 315                 320 atg cat gat ggt gta gtc tta ggc ttc gat cat tca cgg atg gac cgg    1008
Met His Asp Gly Val Val Leu Gly Phe Asp His Ser Arg Met Asp Arg
```

-continued

| | | | | |
|---|---|---|---|---|
| | 325 | 330 | 335 | |
| cca cgg tac acc cag cga ttc tcg agt ccg gtg gtc cgc gtc ttc gat<br>Pro Arg Tyr Thr Gln Arg Phe Ser Ser Pro Val Val Arg Val Phe Asp<br>340 345 350 | | | | 1056 |
| gtt gct cgt ccg gtc agc gcc gac tca tct aac gac cct act cca ctt<br>Val Ala Arg Pro Val Ser Ala Asp Ser Ser Asn Asp Pro Thr Pro Leu<br>355 360 365 | | | | 1104 |
| att cta ctc tcg cag cct cta cag cct cct gac ccc gac tac ggt acg<br>Ile Leu Leu Ser Gln Pro Leu Gln Pro Pro Asp Pro Asp Tyr Gly Thr<br>370 375 380 | | | | 1152 |
| ctt gac gat cgt gat gaa aga gta ttc att gat tac acc gag ggt ggt<br>Leu Asp Asp Arg Asp Glu Arg Val Phe Ile Asp Tyr Thr Glu Gly Gly<br>385 390 395 400 | | | | 1200 |
| ggt tgg tat gcc atg tcg gag gcc acc tac ccg ctt gtc acc ggg aga<br>Gly Trp Tyr Ala Met Ser Glu Ala Thr Tyr Pro Leu Val Thr Gly Arg<br>405 410 415 | | | | 1248 |
| gcc aag atg gct caa tgc tac gaa aaa gat tac ctc cgc cat ggt caa<br>Ala Lys Met Ala Gln Cys Tyr Glu Lys Asp Tyr Leu Arg His Gly Gln<br>420 425 430 | | | | 1296 |
| ccc cta aca agt ctg acc ccg agt cag caa caa gat gca cta gca gga<br>Pro Leu Thr Ser Leu Thr Pro Ser Gln Gln Gln Asp Ala Leu Ala Gly<br>435 440 445 | | | | 1344 |
| gtc cat tct ttg aac ggc cca cgc gtc gtc cgc cgt cac atc ccc agc<br>Val His Ser Leu Asn Gly Pro Arg Val Val Arg Arg His Ile Pro Ser<br>450 455 460 | | | | 1392 |
| att tct ggc ccc tcg tca gcc gat atg tcc aat gac acg cct cgg gag<br>Ile Ser Gly Pro Ser Ser Ala Asp Met Ser Asn Asp Thr Pro Arg Glu<br>465 470 475 480 | | | | 1440 |
| ttg atc tat agc tca tcg gac ttg gca ctg cct ccg gct cta cgc cac<br>Leu Ile Tyr Ser Ser Ser Asp Leu Ala Leu Pro Pro Ala Leu Arg His<br>485 490 495 | | | | 1488 |
| agc acc att ata cgg aag ggc tgg gac aat gcc att gat att ttt gtg<br>Ser Thr Ile Ile Arg Lys Gly Trp Asp Asn Ala Ile Asp Ile Phe Val<br>500 505 510 | | | | 1536 |
| acg ctc ttg ctt ctg ttt ttc ggc acc ttc atc tgg ttc aat tct cat<br>Thr Leu Leu Leu Leu Phe Phe Gly Thr Phe Ile Trp Phe Asn Ser His<br>515 520 525 | | | | 1584 |
| cac att cag gag ctt gct aag cag aag ctg gat ctg aaa aat atc atg<br>His Ile Gln Glu Leu Ala Lys Gln Lys Leu Asp Leu Lys Asn Ile Met<br>530 535 540 | | | | 1632 |
| gcc tcg tac gga cag ccg ccc atg tct acc ccc tca act cca atc gtg<br>Ala Ser Tyr Gly Gln Pro Pro Met Ser Thr Pro Ser Thr Pro Ile Val<br>545 550 555 560 | | | | 1680 |
| gaa gcc cct cat ttg aaa cgc gag gct agc cct aat cgc atg gcg aat<br>Glu Ala Pro His Leu Lys Arg Glu Ala Ser Pro Asn Arg Met Ala Asn<br>565 570 575 | | | | 1728 |
| ctg act gtc gac atg aat gtt tca gga gag cag ccg cag ggt ggt gac<br>Leu Thr Val Asp Met Asn Val Ser Gly Glu Gln Pro Gln Gly Gly Asp<br>580 585 590 | | | | 1776 |
| tcg acg cca agg ccc aag aaa tcc cag aac tct ctt gcg ccc gac aca<br>Ser Thr Pro Arg Pro Lys Lys Ser Gln Asn Ser Leu Ala Pro Asp Thr<br>595 600 605 | | | | 1824 |
| act cca cgc gta cgc atc cgg gaa ccg tct caa ggc cca gat ggc gat<br>Thr Pro Arg Val Arg Ile Arg Glu Pro Ser Gln Gly Pro Asp Gly Asp<br>610 615 620 | | | | 1872 |
| gac gat gtg gac gag ctc aat cta caa gac ggt gaa aag cct aag aag<br>Asp Asp Val Asp Glu Leu Asn Leu Gln Asp Gly Glu Lys Pro Lys Lys<br>625 630 635 640 | | | | 1920 |
| aag gct cgc cgc ggt cgt cgt ggt ggc aag aat cat agg cgg ggc aag<br> | | | | 1968 |

|                                                                                              |      |
|----------------------------------------------------------------------------------------------|------|
| Lys Ala Arg Arg Gly Arg Gly Gly Lys Asn His Arg Arg Gly Lys<br>                   645                   650               655 |      |
| aag ccc aat agc gac agc gaa tcc agg gac ccg gcc gat cgc gtt gtt<br>Lys Pro Asn Ser Asp Ser Glu Ser Arg Asp Pro Ala Asp Arg Val Val<br>              660                   665                 670 | 2016 |
| gat gaa gtg aac aag ctt caa cct cag cct cgc ttg gaa ccc gat gta<br>Asp Glu Val Asn Lys Leu Gln Pro Gln Pro Arg Leu Glu Pro Asp Val<br>        675                   680                 685 | 2064 |
| cag ctg gcc cgg acg gtg tcg cat gag atc atg gaa atg gat ggc gtt<br>Gln Leu Ala Arg Thr Val Ser His Glu Ile Met Glu Met Asp Gly Val<br>   690                   695                 700 | 2112 |
| ctc cag atc ggc cgt ctt agg gtg ttc act gac gtg gtc ctg gga cac<br>Leu Gln Ile Gly Arg Leu Arg Val Phe Thr Asp Val Val Leu Gly His<br>705                   710                 715                 720 | 2160 |
| ggc agc cac ggg acc gtg gtg tat cgg ggc tcg ttc gat gga cgc gac<br>Gly Ser His Gly Thr Val Val Tyr Arg Gly Ser Phe Asp Gly Arg Asp<br>               725                 730                 735 | 2208 |
| gtg gct gtc aag cgc atg ctg gta gaa ttc tat gat att gca tcc cat<br>Val Ala Val Lys Arg Met Leu Val Glu Phe Tyr Asp Ile Ala Ser His<br>        740                   745                 750 | 2256 |
| gaa gtg ggc ctg ttg caa gaa agt gat gac cat ggc aat gtg atc cgg<br>Glu Val Gly Leu Leu Gln Glu Ser Asp Asp His Gly Asn Val Ile Arg<br>             755                   760               765 | 2304 |
| tac tac tgc cga gag cag gct gct ggt ttc ctc tac att gct ttg gag<br>Tyr Tyr Cys Arg Glu Gln Ala Ala Gly Phe Leu Tyr Ile Ala Leu Glu<br>   770                   775                 780 | 2352 |
| ctc tgc ccg gcc tct ttg cag gat gtg gtt gaa cgt cca tca gat ttc<br>Leu Cys Pro Ala Ser Leu Gln Asp Val Val Glu Arg Pro Ser Asp Phe<br>785                   790                 795                 800 | 2400 |
| ccg cag tta gtc cag ggc ggc ttg gac ctg ccg gac gtt ctg cgc cag<br>Pro Gln Leu Val Gln Gly Gly Leu Asp Leu Pro Asp Val Leu Arg Gln<br>                 805                   810               815 | 2448 |
| att gtg gca ggt gtt cgc tat ctt cat tct ctt aag att gtg cac cgc<br>Ile Val Ala Gly Val Arg Tyr Leu His Ser Leu Lys Ile Val His Arg<br>        820                   825                 830 | 2496 |
| gat ctg aag cca cag aac atc ttg gtg gcg atg cct cgc ggg cgt act<br>Asp Leu Lys Pro Gln Asn Ile Leu Val Ala Met Pro Arg Gly Arg Thr<br>             835                   840               845 | 2544 |
| ggt tca cgc tcc ctg cgg ttg ctg atc tcg gat ttc ggc ttg tgt aag<br>Gly Ser Arg Ser Leu Arg Leu Leu Ile Ser Asp Phe Gly Leu Cys Lys<br>850                   855                 860 | 2592 |
| aag ctc gaa gac aac cag agc tcc ttc cgc gca act acg gca cat gcc<br>Lys Leu Glu Asp Asn Gln Ser Ser Phe Arg Ala Thr Thr Ala His Ala<br>865                   870                 875                 880 | 2640 |
| gcg ggt acc tca ggc tgg cga gcc cct gaa ttg ctg gta gac gac gac<br>Ala Gly Thr Ser Gly Trp Arg Ala Pro Glu Leu Leu Val Asp Asp Asp<br>               885                   890               895 | 2688 |
| atg agc ccg gct atg cag ggt agc gag tcc caa cac acc gaa tca tca<br>Met Ser Pro Ala Met Gln Gly Ser Glu Ser Gln His Thr Glu Ser Ser<br>        900                   905                 910 | 2736 |
| gaa cca gct gtg gtg gat cct caa acc aac cgg cgg gct act cga gct<br>Glu Pro Ala Val Val Asp Pro Gln Thr Asn Arg Arg Ala Thr Arg Ala<br>             915                   920               925 | 2784 |
| atc gac atc ttc tct ttg ggc tgc gtc ttt tat tac gtt ctg acg cgg<br>Ile Asp Ile Phe Ser Leu Gly Cys Val Phe Tyr Tyr Val Leu Thr Arg<br>        930                   935                 940 | 2832 |
| ggg tgc cat cct ttt gac aag aat ggc aag ttt atg cgc gag gcc aac<br>Gly Cys His Pro Phe Asp Lys Asn Gly Lys Phe Met Arg Glu Ala Asn<br>945                   950                 955                 960 | 2880 |

-continued

| | |
|---|---|
| att gtc aag ggc aac cac aac ctc gat gag ctg cag cgt ctg ggc gac<br>Ile Val Lys Gly Asn His Asn Leu Asp Glu Leu Gln Arg Leu Gly Asp<br>965 970 975 | 2928 |
| tat gcc tac gag gct gaa gat cta atc cag tcc atg ttg tcg ctt gat<br>Tyr Ala Tyr Glu Ala Glu Asp Leu Ile Gln Ser Met Leu Ser Leu Asp<br>980 985 990 | 2976 |
| cct cga cga cga ccc gat gcg agc gct gtg ttg acg cac ccg ttc ttt<br>Pro Arg Arg Arg Pro Asp Ala Ser Ala Val Leu Thr His Pro Phe Phe<br>995 1000 1005 | 3024 |
| tgg cct cca tct gac cgt ctt agc ttc ctc tgc gat gtc tcg gat<br>Trp Pro Pro Ser Asp Arg Leu Ser Phe Leu Cys Asp Val Ser Asp<br>1010 1015 1020 | 3069 |
| cac ttt gaa ttt gaa ccg cgg gat cct cct tcg gac gcc ctt ttg<br>His Phe Glu Phe Glu Pro Arg Asp Pro Pro Ser Asp Ala Leu Leu<br>1025 1030 1035 | 3114 |
| tgt ctc gag tcg gtc gct cca cga gtg atg ggc ccg gac atg gat<br>Cys Leu Glu Ser Val Ala Pro Arg Val Met Gly Pro Asp Met Asp<br>1040 1045 1050 | 3159 |
| ttc ctg cga cta ctg cca cgg gac ttt aag gat aat ctc ggc aag<br>Phe Leu Arg Leu Leu Pro Arg Asp Phe Lys Asp Asn Leu Gly Lys<br>1055 1060 1065 | 3204 |
| cag cgt aag tac acg gga tcg aag atg tta gat ttg ctg cga gcc<br>Gln Arg Lys Tyr Thr Gly Ser Lys Met Leu Asp Leu Leu Arg Ala<br>1070 1075 1080 | 3249 |
| ctc cgg aac aag cgc aac cat tac aac gac atg ccg gag cat ctc<br>Leu Arg Asn Lys Arg Asn His Tyr Asn Asp Met Pro Glu His Leu<br>1085 1090 1095 | 3294 |
| aag gca cac atc ggc ggg ttg ccc gag ggg tat ctt aat ttt tgg<br>Lys Ala His Ile Gly Gly Leu Pro Glu Gly Tyr Leu Asn Phe Trp<br>1100 1105 1110 | 3339 |
| act gtg cga ttc ccc agt ctt ctc atg agc tgc cac tcc gtc att<br>Thr Val Arg Phe Pro Ser Leu Leu Met Ser Cys His Ser Val Ile<br>1115 1120 1125 | 3384 |
| gtg gag ttg cgt ttg acg cgg tcc gac cgt ttc aag cgc tac ttc<br>Val Glu Leu Arg Leu Thr Arg Ser Asp Arg Phe Lys Arg Tyr Phe<br>1130 1135 1140 | 3429 |
| acg gcg act gac tag<br>Thr Ala Thr Asp<br>1145 | 3444 |

<210> SEQ ID NO 19
<211> LENGTH: 1147
<212> TYPE: PRT
<213> ORGANISM: artificial sequence
<220> FEATURE:
<223> OTHER INFORMATION: Synthetic Construct

<400> SEQUENCE: 19

Met Arg Trp Arg Leu Pro Gly Ala Arg Ser Thr Leu Pro Ala Ser Val
1               5                   10                  15

Ala Leu Leu Leu Leu Pro Val Leu Val Ala Pro Gln Gln Trp His Glu
            20                  25                  30

His Gln His Glu Leu Ser Ser Thr Val Ser Val Pro Leu Arg Pro Thr
        35                  40                  45

Gly Phe Thr Ser Gly Val Asp Thr Pro Pro Ser Phe Asp Val Lys Ser
    50                  55                  60

Asn Asp Ala Ser Ala Leu Ala Thr Leu Ala Leu Ala Gly Ser Gly Arg
65                  70                  75                  80

Thr Val Arg Thr Pro Pro Ala Gln Ala Ser Ser Ser Thr Ala Gly Leu
                85                  90                  95

```
Ala Pro Gln Leu His Ala Arg Ser Leu Gln Asp Trp Glu Val Glu Asp
            100                 105                 110
Phe Val Leu Leu Ala Thr Val Asp Gly Ser Ile His Ala Arg Asp Arg
            115                 120                 125
Lys Thr Gly Ala Ala Arg Trp Ala Leu Glu Val Pro Ser Ser Pro Met
        130                 135                 140
Val Glu Ser Leu Tyr His Arg Ala Asn Arg Ser Ser Phe Asp Arg Ala
145                 150                 155                 160
Gln Pro Glu Asp Asp Phe Ile Trp Ile Val Glu Pro Ser Gln Gly Gly
                    165                 170                 175
Ser Leu Tyr Ile Tyr Ser Ser Gly Pro Glu Ala Gly Leu Gln Lys Leu
            180                 185                 190
Gly Leu Thr Val Lys Glu Leu Val Asp Glu Thr Pro Tyr Ser Gly Thr
            195                 200                 205
Asp Pro Ala Val Thr Tyr Thr Ala Arg Lys Glu Thr Thr Leu Tyr Thr
        210                 215                 220
Ile Asp Ala Arg Thr Gly Asn Ile Leu Arg Val Phe Ser Ser Arg Gly
225                 230                 235                 240
Pro Ile Ser Ser Gly Gln Glu Cys Arg Lys Val Asp Gly Leu Asp Val
            245                 250                 255
Asp Met Glu Glu Cys Glu Ser Pro Ser Gly Thr Leu Val Leu Gly Arg
            260                 265                 270
Val Glu Tyr Thr Val Ala Ile Gln Asn Thr Glu Thr Gly Asp Pro Ile
        275                 280                 285
Cys Thr Leu Lys Tyr Ser Glu Trp Thr Ala Asn Asn Arg Asp Met Asp
        290                 295                 300
Leu Gln Ser Gln Tyr Leu Arg Thr Met Asp Gln Ser His Ile Tyr Ser
305                 310                 315                 320
Met His Asp Gly Val Val Leu Gly Phe Asp His Ser Arg Met Asp Arg
                    325                 330                 335
Pro Arg Tyr Thr Gln Arg Phe Ser Ser Pro Val Val Arg Val Phe Asp
            340                 345                 350
Val Ala Arg Pro Val Ser Ala Asp Ser Ser Asn Asp Pro Thr Pro Leu
            355                 360                 365
Ile Leu Leu Ser Gln Pro Leu Gln Pro Pro Asp Pro Asp Tyr Gly Thr
        370                 375                 380
Leu Asp Asp Arg Asp Glu Arg Val Phe Ile Asp Tyr Thr Glu Gly Gly
385                 390                 395                 400
Gly Trp Tyr Ala Met Ser Glu Ala Thr Tyr Pro Leu Val Thr Gly Arg
            405                 410                 415
Ala Lys Met Ala Gln Cys Tyr Glu Lys Asp Tyr Leu Arg His Gly Gln
        420                 425                 430
Pro Leu Thr Ser Leu Thr Pro Ser Gln Gln Gln Asp Ala Leu Ala Gly
            435                 440                 445
Val His Ser Leu Asn Gly Pro Arg Val Val Arg His Ile Pro Ser
        450                 455                 460
Ile Ser Gly Pro Ser Ser Ala Asp Met Ser Asn Asp Thr Pro Arg Glu
465                 470                 475                 480
Leu Ile Tyr Ser Ser Ser Asp Leu Ala Leu Pro Pro Ala Leu Arg His
                    485                 490                 495
Ser Thr Ile Ile Arg Lys Gly Trp Asp Asn Ala Ile Asp Ile Phe Val
            500                 505                 510
```

```
Thr Leu Leu Leu Leu Phe Phe Gly Thr Phe Ile Trp Phe Asn Ser His
            515                 520                 525
His Ile Gln Glu Leu Ala Lys Gln Lys Leu Asp Leu Lys Asn Ile Met
530                 535                 540
Ala Ser Tyr Gly Gln Pro Pro Met Ser Thr Pro Ser Thr Pro Ile Val
545                 550                 555                 560
Glu Ala Pro His Leu Lys Arg Glu Ala Ser Pro Asn Arg Met Ala Asn
                565                 570                 575
Leu Thr Val Asp Met Asn Val Ser Gly Glu Gln Pro Gln Gly Gly Asp
                580                 585                 590
Ser Thr Pro Arg Pro Lys Lys Ser Gln Asn Ser Leu Ala Pro Asp Thr
            595                 600                 605
Thr Pro Arg Val Arg Ile Arg Glu Pro Ser Gln Gly Pro Asp Gly Asp
        610                 615                 620
Asp Asp Val Asp Glu Leu Asn Leu Gln Asp Gly Glu Lys Pro Lys Lys
625                 630                 635                 640
Lys Ala Arg Arg Gly Arg Gly Gly Lys Asn His Arg Arg Gly Lys
                645                 650                 655
Lys Pro Asn Ser Asp Ser Glu Ser Arg Asp Pro Ala Asp Arg Val Val
                660                 665                 670
Asp Glu Val Asn Lys Leu Gln Pro Gln Pro Arg Leu Glu Pro Asp Val
                675                 680                 685
Gln Leu Ala Arg Thr Val Ser His Glu Ile Met Glu Met Asp Gly Val
        690                 695                 700
Leu Gln Ile Gly Arg Leu Arg Val Phe Thr Asp Val Val Leu Gly His
705                 710                 715                 720
Gly Ser His Gly Thr Val Val Tyr Arg Gly Ser Phe Asp Gly Arg Asp
                725                 730                 735
Val Ala Val Lys Arg Met Leu Val Glu Phe Tyr Asp Ile Ala Ser His
                740                 745                 750
Glu Val Gly Leu Leu Gln Glu Ser Asp His Gly Asn Val Ile Arg
        755                 760                 765
Tyr Tyr Cys Arg Glu Gln Ala Ala Gly Phe Leu Tyr Ile Ala Leu Glu
770                 775                 780
Leu Cys Pro Ala Ser Leu Gln Asp Val Val Glu Arg Pro Ser Asp Phe
785                 790                 795                 800
Pro Gln Leu Val Gln Gly Gly Leu Asp Leu Pro Asp Val Leu Arg Gln
                805                 810                 815
Ile Val Ala Gly Val Arg Tyr Leu His Ser Leu Lys Ile Val His Arg
                820                 825                 830
Asp Leu Lys Pro Gln Asn Ile Leu Val Ala Met Pro Arg Gly Arg Thr
                835                 840                 845
Gly Ser Arg Ser Leu Arg Leu Leu Ile Ser Asp Phe Gly Leu Cys Lys
        850                 855                 860
Lys Leu Glu Asp Asn Gln Ser Ser Phe Arg Ala Thr Thr Ala His Ala
865                 870                 875                 880
Ala Gly Thr Ser Gly Trp Arg Ala Pro Glu Leu Leu Val Asp Asp
                885                 890                 895
Met Ser Pro Ala Met Gln Gly Ser Glu Ser Gln His Thr Glu Ser Ser
                900                 905                 910
Glu Pro Ala Val Val Asp Pro Gln Thr Asn Arg Arg Ala Thr Arg Ala
        915                 920                 925
Ile Asp Ile Phe Ser Leu Gly Cys Val Phe Tyr Tyr Val Leu Thr Arg
```

-continued

```
                930             935             940
Gly Cys His Pro Phe Asp Lys Asn Gly Lys Phe Met Arg Glu Ala Asn
945                 950             955             960

Ile Val Lys Gly Asn His Asn Leu Asp Glu Leu Gln Arg Leu Gly Asp
                965             970             975

Tyr Ala Tyr Glu Ala Glu Asp Leu Ile Gln Ser Met Leu Ser Leu Asp
            980             985             990

Pro Arg Arg Arg Pro Asp Ala Ser Ala Val Leu Thr His Pro Phe Phe
        995             1000            1005

Trp Pro Pro Ser Asp Arg Leu Ser Phe Leu Cys Asp Val Ser Asp
    1010            1015            1020

His Phe Glu Phe Glu Pro Arg Asp Pro Ser Asp Ala Leu Leu
    1025            1030            1035

Cys Leu Glu Ser Val Ala Pro Arg Val Met Gly Pro Asp Met Asp
    1040            1045            1050

Phe Leu Arg Leu Pro Arg Asp Phe Lys Asp Asn Leu Gly Lys
    1055            1060            1065

Gln Arg Lys Tyr Thr Gly Ser Lys Met Leu Asp Leu Leu Arg Ala
    1070            1075            1080

Leu Arg Asn Lys Arg Asn His Tyr Asn Asp Met Pro Glu His Leu
    1085            1090            1095

Lys Ala His Ile Gly Gly Leu Pro Glu Gly Tyr Leu Asn Phe Trp
    1100            1105            1110

Thr Val Arg Phe Pro Ser Leu Leu Met Ser Cys His Ser Val Ile
    1115            1120            1125

Val Glu Leu Arg Leu Thr Arg Ser Asp Arg Phe Lys Arg Tyr Phe
    1130            1135            1140

Thr Ala Thr Asp
    1145

<210> SEQ ID NO 20
<211> LENGTH: 19
<212> TYPE: DNA
<213> ORGANISM: artificial sequence
<220> FEATURE:
<223> OTHER INFORMATION: Primer HTJP-697

<400> SEQUENCE: 20
cagcagtggc atgaacatc                                                 19

<210> SEQ ID NO 21
<211> LENGTH: 19
<212> TYPE: DNA
<213> ORGANISM: artificial sequence
<220> FEATURE:
<223> OTHER INFORMATION: Primer HTJP-698

<400> SEQUENCE: 21
aggactagag tacccgaag                                                 19
```